United States Patent
Marraffini et al.

(10) Patent No.: US 11,377,645 B2
(45) Date of Patent: Jul. 5, 2022

(54) COMPOSITIONS AND METHODS USING CAS9 WITH ENHANCED SPACER ACQUISITION FUNCTION

(71) Applicant: The Rockefeller University, New York, NY (US)

(72) Inventors: Luciano Marraffini, Brooklyn, NY (US); Robert Heller, New York, NY (US); David Bikard, Paris (FR)

(73) Assignee: The Rockefeller University, New York, NY (US)

( * ) Notice: Subject to any disclaimer, the term of this patent is extended or adjusted under 35 U.S.C. 154(b) by 95 days.

(21) Appl. No.: 16/470,195

(22) PCT Filed: Dec. 18, 2017

(86) PCT No.: PCT/US2017/066937
§ 371 (c)(1),
(2) Date: Jun. 14, 2019

(87) PCT Pub. No.: WO2018/112451
PCT Pub. Date: Jun. 21, 2018

(65) Prior Publication Data
US 2019/0330606 A1  Oct. 31, 2019

Related U.S. Application Data

(60) Provisional application No. 62/435,406, filed on Dec. 16, 2016.

(51) Int. Cl.
| | | |
|---|---|---|
| *C12N 9/22* | (2006.01) | |
| *A23C 9/123* | (2006.01) | |
| *C12N 15/74* | (2006.01) | |
| *C12G 1/00* | (2019.01) | |

(52) U.S. Cl.
CPC .......... *C12N 9/22* (2013.01); *A23C 9/123* (2013.01); *C12G 1/00* (2013.01); *C12N 15/74* (2013.01); *C12N 2310/20* (2017.05); *C12N 2795/00011* (2013.01); *C12N 2820/55* (2013.01)

(58) Field of Classification Search
CPC .............. C12N 9/22; C12N 2310/20; C12N 2795/00011; C07H 21/04
USPC .............. 424/184.1, 185.1; 536/23.1, 23.2
See application file for complete search history.

(56) References Cited

U.S. PATENT DOCUMENTS

2016/0319261 A1  11/2016  Joung et al.

FOREIGN PATENT DOCUMENTS

WO  2018/149888 A1  8/2018

OTHER PUBLICATIONS

Nishimasu, H., et al., Crystal Structure of Cas9 in Complex with Guide RNA and Target DNA, Cell, Feb. 27, 2014, vol. 156, pp. 935-949.
Steffens, D.L. and Williams, G.K., Efficient Site-Directed Saturation Mutagenesis Using Degenerate Oligonucleotides, Journal of Biomolecular Techniques, Jul. 2007, vol. 18, No. 3, pp. 147-149.
Lia-Baldini, A.S., et al., A molecular approach to dominance in hypophosphatasia, Hum Genet, Jul. 3, 2001, vol. 109, pp. 99-108.
Esvelt, K.M., et al., Orthogonal Cas9 Proteins for RNA-GUided Gene Regulation and Editing, Nat Methods, Nov. 2013, vol. 10, No. 11, pp. 1116-1121.
Zhang, Y., et al., Comparison of non-canonical PAMs for CRISPR/Cas9-mediated DNA cleavage in human cells, Scientific Reports, Jun. 23, 2014, vol. 4, pp. 1-5.
Heler, R., et al., Mutations is Cas9 enhance the rate of acquisition of viral spacer sequences during the CRISPR-Cas immune response, Mol Cell, Jan. 5, 2017, vol. 65, No. 1, pp. 168-175.
Wei, Y. et al., Cas9 function and host genome sampling in Type II-A CRISPR-Cas adaptation, Genes and Development, Feb. 15, 2015, vol. 29, No. 4, pp. 356-361.
Heler, R. et al., Cas9 specifies functional viral targets during CRISPR-Cas adaptation, Nature, Feb. 18, 2015, vol. 519, No. 7542, pp. 199-202.
Anders, C. et al., Structural basis of PAM-dependent target DNA recognition by the Cas9 endonuclease, Nature, Jul. 27, 2014, vol. 513, No. 7519, pp. 569-573.
Jinek, M. et al., Structures of Cas9 Endonucleases Reveal RNA-Mediated Conformational Activation, Science, Mar. 14, 2014, vol. 343, No. 6176, pp. 1-28.

*Primary Examiner* — Jennifer E Graser
(74) *Attorney, Agent, or Firm* — Hodgson Russ LLP

(57) ABSTRACT

Provided are Cas9 enzymes that have mutations that enhance their properties, relative to un-mutated Cas9. The altered Cas9 enzymes exhibit i) an increased rate of spacer acquisition, or ii) increased cleavage efficiency of targets with NAG PAMs, or a combination of i) and ii). The altered Cas9 enzymes comprise an amino acid substitution of 1473 and K500 in a *Streptococcus pyogenes* or similar Cas9 enzyme. Also provided are polynucleotides, including expression vectors that encode the Cas9 enzymes, cells that contain the polynucleotides, and methods of making and using such cells. The disclosure includes tagging, or labelling bacteria, and for enhancing phage acquired immunity in bacteria, such as those used in industrial processes, including the food and beverage industry, such as the dairy industry. The food products are also included.

16 Claims, 16 Drawing Sheets
(10 of 16 Drawing Sheet(s) Filed in Color)
Specification includes a Sequence Listing.

D

K500

SEQUENCE LISTING

```
<160> NUMBER OF SEQ ID NOS: 155

<210> SEQ ID NO 1
<211> LENGTH: 1368
<212> TYPE: PRT
<213> ORGANISM: Streptococcus pyogenes

<400> SEQUENCE: 1

Met Asp Lys Lys Tyr Ser Ile Gly Leu Asp Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175
```

```
Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
            245                 250                 255

Asp Leu Ala Glu Asp Ala Lys Leu Gln Leu Ser Lys Asp Thr Tyr Asp
        260                 265                 270

Asp Asp Leu Asp Asn Leu Leu Ala Gln Ile Gly Asp Gln Tyr Ala Asp
    275                 280                 285

Leu Phe Leu Ala Ala Lys Asn Leu Ser Asp Ala Ile Leu Leu Ser Asp
290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
            325                 330                 335

Ala Leu Val Arg Gln Gln Leu Pro Glu Lys Tyr Lys Glu Ile Phe Phe
        340                 345                 350

Asp Gln Ser Lys Asn Gly Tyr Ala Gly Tyr Ile Asp Gly Gly Ala Ser
    355                 360                 365

Gln Glu Glu Phe Tyr Lys Phe Ile Lys Pro Ile Leu Glu Lys Met Asp
370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
            405                 410                 415

Gly Glu Leu His Ala Ile Leu Arg Arg Gln Glu Asp Phe Tyr Pro Phe
        420                 425                 430

Leu Lys Asp Asn Arg Glu Lys Ile Glu Lys Ile Leu Thr Phe Arg Ile
    435                 440                 445

Pro Tyr Tyr Val Gly Pro Leu Ala Arg Gly Asn Ser Arg Phe Ala Trp
450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
            485                 490                 495

Asn Phe Asp Lys Asn Leu Pro Asn Glu Lys Val Leu Pro Lys His Ser
        500                 505                 510

Leu Leu Tyr Glu Tyr Phe Thr Val Tyr Asn Glu Leu Thr Lys Val Lys
    515                 520                 525

Tyr Val Thr Glu Gly Met Arg Lys Pro Ala Phe Leu Ser Gly Glu Gln
530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
            565                 570                 575

Ser Val Glu Ile Ser Gly Val Glu Asp Arg Phe Asn Ala Ser Leu Gly
        580                 585                 590

Thr Tyr His Asp Leu Leu Lys Ile Ile Lys Asp Lys Asp Phe Leu Asp
```

```
                595                 600                 605
Asn Glu Glu Asn Glu Asp Ile Leu Glu Asp Ile Val Leu Thr Leu Thr
610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
                660                 665                 670

Lys Gln Ser Gly Lys Thr Ile Leu Asp Phe Leu Lys Ser Asp Gly Phe
            675                 680                 685

Ala Asn Arg Asn Phe Met Gln Leu Ile His Asp Asp Ser Leu Thr Phe
690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
            740                 745                 750

Arg His Lys Pro Glu Asn Ile Val Ile Glu Met Ala Arg Glu Asn Gln
            755                 760                 765

Thr Thr Gln Lys Gly Gln Lys Asn Ser Arg Glu Arg Met Lys Arg Ile
770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
            820                 825                 830

Leu Ser Asp Tyr Asp Val Asp His Ile Val Pro Gln Ser Phe Leu Lys
        835                 840                 845

Asp Asp Ser Ile Asp Asn Lys Val Leu Thr Arg Ser Asp Lys Asn Arg
850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
            900                 905                 910

Lys Ala Gly Phe Ile Lys Arg Gln Leu Val Glu Thr Arg Gln Ile Thr
        915                 920                 925

Lys His Val Ala Gln Ile Leu Asp Ser Arg Met Asn Thr Lys Tyr Asp
        930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
                965                 970                 975

Glu Ile Asn Asn Tyr His His Ala His Asp Ala Tyr Leu Asn Ala Val
            980                 985                 990

Val Gly Thr Ala Leu Ile Lys Lys Tyr Pro Lys Leu Glu Ser Glu Phe
        995                 1000                1005

Val Tyr Gly Asp Tyr Lys Val Tyr Asp Val Arg Lys Met Ile Ala
    1010                1015                1020
```

| | | | | | | | | | | |
|---|---|---|---|---|---|---|---|---|---|---|
| Lys | Ser | Glu | Gln | Glu | Ile | Gly | Lys | Ala | Thr | Ala | Lys | Tyr | Phe | Phe |
| | 1025 | | | | 1030 | | | | 1035 | |

Tyr Ser Asn Ile Met Asn Phe Phe Lys Thr Glu Ile Thr Leu Ala
1040                    1045                    1050

Asn Gly Glu Ile Arg Lys Arg Pro Leu Ile Glu Thr Asn Gly Glu
1055                    1060                    1065

Thr Gly Glu Ile Val Trp Asp Lys Gly Arg Asp Phe Ala Thr Val
1070                    1075                    1080

Arg Lys Val Leu Ser Met Pro Gln Val Asn Ile Val Lys Lys Thr
1085                    1090                    1095

Glu Val Gln Thr Gly Gly Phe Ser Lys Glu Ser Ile Leu Pro Lys
1100                    1105                    1110

Arg Asn Ser Asp Lys Leu Ile Ala Arg Lys Lys Asp Trp Asp Pro
1115                    1120                    1125

Lys Lys Tyr Gly Gly Phe Asp Ser Pro Thr Val Ala Tyr Ser Val
1130                    1135                    1140

Leu Val Val Ala Lys Val Glu Lys Gly Lys Ser Lys Lys Leu Lys
1145                    1150                    1155

Ser Val Lys Glu Leu Leu Gly Ile Thr Ile Met Glu Arg Ser Ser
1160                    1165                    1170

Phe Glu Lys Asn Pro Ile Asp Phe Leu Glu Ala Lys Gly Tyr Lys
1175                    1180                    1185

Glu Val Lys Lys Asp Leu Ile Ile Lys Leu Pro Lys Tyr Ser Leu
1190                    1195                    1200

Phe Glu Leu Glu Asn Gly Arg Lys Arg Met Leu Ala Ser Ala Gly
1205                    1210                    1215

Glu Leu Gln Lys Gly Asn Glu Leu Ala Leu Pro Ser Lys Tyr Val
1220                    1225                    1230

Asn Phe Leu Tyr Leu Ala Ser His Tyr Glu Lys Leu Lys Gly Ser
1235                    1240                    1245

Pro Glu Asp Asn Glu Gln Lys Gln Leu Phe Val Glu Gln His Lys
1250                    1255                    1260

His Tyr Leu Asp Glu Ile Ile Glu Gln Ile Ser Glu Phe Ser Lys
1265                    1270                    1275

Arg Val Ile Leu Ala Asp Ala Asn Leu Asp Lys Val Leu Ser Ala
1280                    1285                    1290

Tyr Asn Lys His Arg Asp Lys Pro Ile Arg Glu Gln Ala Glu Asn
1295                    1300                    1305

Ile Ile His Leu Phe Thr Leu Thr Asn Leu Gly Ala Pro Ala Ala
1310                    1315                    1320

Phe Lys Tyr Phe Asp Thr Thr Ile Asp Arg Lys Arg Tyr Thr Ser
1325                    1330                    1335

Thr Lys Glu Val Leu Asp Ala Thr Leu Ile His Gln Ser Ile Thr
1340                    1345                    1350

Gly Leu Tyr Glu Thr Arg Ile Asp Leu Ser Gln Leu Gly Gly Asp
1355                    1360                    1365

<210> SEQ ID NO 2
<211> LENGTH: 30
<212> TYPE: DNA
<213> ORGANISM: Streptococcus pyogenes

<400> SEQUENCE: 2
ataaataaaa aagttactac tcacacacta                                      30

<210> SEQ ID NO 3
<211> LENGTH: 31
<212> TYPE: DNA
<213> ORGANISM: Streptococcus pyogenes

<400> SEQUENCE: 3
cgaactagga agaaaaatcg ccatcaattc a                                    31

<210> SEQ ID NO 4
<211> LENGTH: 30
<212> TYPE: DNA
<213> ORGANISM: Streptococcus pyogenes

<400> SEQUENCE: 4
aatagagata ctttatctaa catgatacac                                      30

<210> SEQ ID NO 5
<211> LENGTH: 30
<212> TYPE: DNA
<213> ORGANISM: Streptococcus pyogenes

<400> SEQUENCE: 5
tgatacacgg gagaacaaaa ccatcctacc                                      30

<210> SEQ ID NO 6
<211> LENGTH: 30
<212> TYPE: DNA
<213> ORGANISM: Streptococcus pyogenes

<400> SEQUENCE: 6
tgatacacgg gagaacaaaa ccatcctacc                                      30

<210> SEQ ID NO 7
<211> LENGTH: 30
<212> TYPE: DNA
<213> ORGANISM: Streptococcus pyogenes

<400> SEQUENCE: 7
gagaacaaaa ccatcctacc cggtaataaa                                      30

<210> SEQ ID NO 8
<211> LENGTH: 31
<212> TYPE: DNA
<213> ORGANISM: Streptococcus pyogenes

<400> SEQUENCE: 8
tttattttgc gttagaattg acacctcaag a                                    31

<210> SEQ ID NO 9
<211> LENGTH: 31
<212> TYPE: DNA
<213> ORGANISM: Streptococcus pyogenes

<400> SEQUENCE: 9
tttattttgc gttagaattg acacctcaag a                                    31

<210> SEQ ID NO 10
<211> LENGTH: 31
<212> TYPE: DNA
<213> ORGANISM: Streptococcus pyogenes

<400> SEQUENCE: 10

```
tttattttgc gttagaattg acacctcaag a                                31

<210> SEQ ID NO 11
<211> LENGTH: 30
<212> TYPE: DNA
<213> ORGANISM: Streptococcus pyogenes

<400> SEQUENCE: 11
tttagcgata ttaattatgc tcgtaagaat                                  30

<210> SEQ ID NO 12
<211> LENGTH: 30
<212> TYPE: DNA
<213> ORGANISM: Streptococcus pyogenes

<400> SEQUENCE: 12
agtattggaa tctgatgaat attcatctct                                  30

<210> SEQ ID NO 13
<211> LENGTH: 31
<212> TYPE: DNA
<213> ORGANISM: Streptococcus pyogenes

<400> SEQUENCE: 13
aaaaatgttt taacacctat taacgtagta t                                31

<210> SEQ ID NO 14
<211> LENGTH: 31
<212> TYPE: DNA
<213> ORGANISM: Streptococcus pyogenes

<400> SEQUENCE: 14
aatattcatc agattccaat actacgttaa t                                31

<210> SEQ ID NO 15
<211> LENGTH: 30
<212> TYPE: DNA
<213> ORGANISM: Streptococcus pyogenes

<400> SEQUENCE: 15
ttcttcgcct ctatatgtgt tttctggtgt                                  30

<210> SEQ ID NO 16
<211> LENGTH: 32
<212> TYPE: DNA
<213> ORGANISM: Streptococcus pyogenes

<400> SEQUENCE: 16 acaaatttt cttcgcctct atatgtgttt tc                                32

<210> SEQ ID NO 17
<211> LENGTH: 31
<212> TYPE: DNA
<213> ORGANISM: Streptococcus pyogenes

<400> SEQUENCE: 17
ccaatttaga aatattaatc agagtgcctg t                                31

<210> SEQ ID NO 18
<211> LENGTH: 30
<212> TYPE: DNA
<213> ORGANISM: Streptococcus pyogenes

<400> SEQUENCE: 18
```

-continued agaaaattta tacattgatt attcaccaac                                30

<210> SEQ ID NO 19
<211> LENGTH: 30
<212> TYPE: DNA
<213> ORGANISM: Streptococcus pyogenes

<400> SEQUENCE: 19
gctaagactg tgaagcataa tactgctact                                30

<210> SEQ ID NO 20
<211> LENGTH: 30
<212> TYPE: DNA
<213> ORGANISM: Streptococcus pyogenes

<400> SEQUENCE: 20
gctaagactg tgaagcataa tactgctact                                30

<210> SEQ ID NO 21
<211> LENGTH: 30
<212> TYPE: DNA
<213> ORGANISM: Streptococcus pyogenes

<400> SEQUENCE: 21
ttttaagcta ttcattttaa aaggtcatat                                30

<210> SEQ ID NO 22
<211> LENGTH: 30
<212> TYPE: DNA
<213> ORGANISM: Streptococcus pyogenes

<400> SEQUENCE: 22
gtgttctctt caatccattc atctattgct                                30

<210> SEQ ID NO 23
<211> LENGTH: 30
<212> TYPE: DNA
<213> ORGANISM: Streptococcus pyogenes

<400> SEQUENCE: 23
atgaatggat tgaagagaac acagacgaac                                30

<210> SEQ ID NO 24
<211> LENGTH: 30
<212> TYPE: DNA
<213> ORGANISM: Streptococcus pyogenes

<400> SEQUENCE: 24
ggagtaacta atatctgaat tgttatcagt                                30

<210> SEQ ID NO 25
<211> LENGTH: 30
<212> TYPE: DNA
<213> ORGANISM: Streptococcus pyogenes

<400> SEQUENCE: 25
attagttact ccacaaatag aaatagagct                                30

<210> SEQ ID NO 26
<211> LENGTH: 31
<212> TYPE: DNA
<213> ORGANISM: Streptococcus pyogenes -continued

<400> SEQUENCE: 26
ccacaaatag aaatagagct agggagttta a                              31

<210> SEQ ID NO 27
<211> LENGTH: 30
<212> TYPE: DNA
<213> ORGANISM: Streptococcus pyogenes

<400> SEQUENCE: 27
tagttttttg agtatgctta cttttcttg                                 30

<210> SEQ ID NO 28
<211> LENGTH: 31
<212> TYPE: DNA
<213> ORGANISM: Streptococcus pyogenes

<400> SEQUENCE: 28
acgaaagcgt ctttatctct tgtagcaaac g                              31

<210> SEQ ID NO 29
<211> LENGTH: 31
<212> TYPE: DNA
<213> ORGANISM: Streptococcus pyogenes

<400> SEQUENCE: 29
aaataagtct aaaaaaccaa cgtttaatga t                              31

<210> SEQ ID NO 30
<211> LENGTH: 31
<212> TYPE: DNA
<213> ORGANISM: Streptococcus pyogenes

<400> SEQUENCE: 30
aaataagtct aaaaaaccaa cgtttaatga t                              31

<210> SEQ ID NO 31
<211> LENGTH: 29
<212> TYPE: DNA
<213> ORGANISM: Streptococcus pyogenes

<400> SEQUENCE: 31
gaacgaattg tcagtatgta cagattaat                                 29

<210> SEQ ID NO 32
<211> LENGTH: 31
<212> TYPE: DNA
<213> ORGANISM: Streptococcus pyogenes

<400> SEQUENCE: 32
aagaagaata caaattccac tttgttatta c                              31

<210> SEQ ID NO 33
<211> LENGTH: 31
<212> TYPE: DNA
<213> ORGANISM: Streptococcus pyogenes

<400> SEQUENCE: 33
gcattacgga cgtagtagaa gcaattagaa a                              31

<210> SEQ ID NO 34
<211> LENGTH: 31
<212> TYPE: DNA
<213> ORGANISM: Streptococcus pyogenes

```
<400> SEQUENCE: 34
aaaaacaatt gattgaatta gttactcgat t                                31

<210> SEQ ID NO 35
<211> LENGTH: 30
<212> TYPE: DNA
<213> ORGANISM: Streptococcus pyogenes

<400> SEQUENCE: 35
tagcttagat tttgatacca atgatcttat                                  30

<210> SEQ ID NO 36
<211> LENGTH: 30
<212> TYPE: DNA
<213> ORGANISM: Streptococcus pyogenes

<400> SEQUENCE: 36
tagcttagat tttgatacca atgatcttat                                  30

<210> SEQ ID NO 37
<211> LENGTH: 30
<212> TYPE: DNA
<213> ORGANISM: Streptococcus pyogenes

<400> SEQUENCE: 37 cggattttc atttattaaa ccttacaaaa                                   30

<210> SEQ ID NO 38
<211> LENGTH: 30
<212> TYPE: DNA
<213> ORGANISM: Streptococcus pyogenes

<400> SEQUENCE: 38
tggatatgac gaccaagatt tagcgtttta                                  30

<210> SEQ ID NO 39
<211> LENGTH: 31
<212> TYPE: DNA
<213> ORGANISM: Streptococcus pyogenes

<400> SEQUENCE: 39
ataacgacgg tacttattcc gtcgttgcta c                                31

<210> SEQ ID NO 40
<211> LENGTH: 30
<212> TYPE: DNA
<213> ORGANISM: Streptococcus pyogenes

<400> SEQUENCE: 40
taatacaggt ttttacaaaa gctttaccat                                  30

<210> SEQ ID NO 41
<211> LENGTH: 30
<212> TYPE: DNA
<213> ORGANISM: Streptococcus pyogenes

<400> SEQUENCE: 41
ctttaaatgt tttaaaagaa tagcatcatt                                  30

<210> SEQ ID NO 42
<211> LENGTH: 30
<212> TYPE: DNA
```

<213> ORGANISM: Artificial Sequence
<220> FEATURE:
<223> OTHER INFORMATION: Spacer sequence acquired by hCas9-expressing cells

<400> SEQUENCE: 42
aatagagata ctttatctaa catgatacac                                    30

<210> SEQ ID NO 43
<211> LENGTH: 30
<212> TYPE: DNA
<213> ORGANISM: Artificial Sequence
<220> FEATURE:
<223> OTHER INFORMATION: Spacer sequence acquired by hCas9-expressing cells

<400> SEQUENCE: 43
tgatacacgg gagaacaaaa ccatcctacc                                    30

<210> SEQ ID NO 44
<211> LENGTH: 30
<212> TYPE: DNA
<213> ORGANISM: Artificial Sequence
<220> FEATURE:
<223> OTHER INFORMATION: Spacer sequence acquired by hCas9-expressing cells

<400> SEQUENCE: 44
gagaacaaaa ccatcctacc cggtaataaa                                    30

<210> SEQ ID NO 45
<211> LENGTH: 30
<212> TYPE: DNA
<213> ORGANISM: Artificial Sequence
<220> FEATURE:
<223> OTHER INFORMATION: Spacer sequence acquired by hCas9-expressing cells

<400> SEQUENCE: 45
agtattggaa tctgatgaat attcatctct                                    30

<210> SEQ ID NO 46
<211> LENGTH: 31
<212> TYPE: DNA
<213> ORGANISM: Artificial Sequence
<220> FEATURE:
<223> OTHER INFORMATION: Spacer sequence acquired by hCas9-expressing cells

<400> SEQUENCE: 46
aaaaatgttt taacacctat taacgtagta t                                  31

<210> SEQ ID NO 47
<211> LENGTH: 31
<212> TYPE: DNA
<213> ORGANISM: Artificial Sequence
<220> FEATURE:
<223> OTHER INFORMATION: Spacer sequence acquired by hCas9-expressing cells

<400> SEQUENCE: 47
aatattcatc agattccaat actacgttaa t                                  31

<210> SEQ ID NO 48
<211> LENGTH: 30
<212> TYPE: DNA
<213> ORGANISM: Artificial Sequence

```
<220> FEATURE:
<223> OTHER INFORMATION: Spacer sequence acquired by hCas9-expressing
      cells

<400> SEQUENCE: 48
ttcttcgcct ctatatgtgt tttctggtgt                                       30

<210> SEQ ID NO 49
<211> LENGTH: 31
<212> TYPE: DNA
<213> ORGANISM: Artificial Sequence
<220> FEATURE:
<223> OTHER INFORMATION: Spacer sequence acquired by hCas9-expressing
      cells

<400> SEQUENCE: 49
aaataagtct aaaaaaccaa cgtttaatga t                                     31

<210> SEQ ID NO 50
<211> LENGTH: 30
<212> TYPE: DNA
<213> ORGANISM: Artificial Sequence
<220> FEATURE:
<223> OTHER INFORMATION: Spacer sequence acquired by hCas9-expressing
      cells

<400> SEQUENCE: 50
aataagatca ttggtatcaa aatctaagct                                       30

<210> SEQ ID NO 51
<211> LENGTH: 30
<212> TYPE: DNA
<213> ORGANISM: Artificial Sequence
<220> FEATURE:
<223> OTHER INFORMATION: Spacer sequence acquired by hCas9-expressing
      cells

<400> SEQUENCE: 51 cggattttc atttattaaa ccttacaaaa                                        30

<210> SEQ ID NO 52
<211> LENGTH: 30
<212> TYPE: DNA
<213> ORGANISM: Artificial Sequence
<220> FEATURE:
<223> OTHER INFORMATION: Spacer sequences acquired by hCas9-expressing
      cells

<400> SEQUENCE: 52 cggattttc atttattaaa ccttacaaaa                                        30

<210> SEQ ID NO 53
<211> LENGTH: 30
<212> TYPE: DNA
<213> ORGANISM: Artificial Sequence
<220> FEATURE:
<223> OTHER INFORMATION: Spacer sequence acquired by hCas9-expressing
      cells

<400> SEQUENCE: 53
cgacataacg ctaatacatg tttgtcatag                                       30

<210> SEQ ID NO 54
<211> LENGTH: 30
<212> TYPE: DNA
<213> ORGANISM: Artificial Sequence
<220> FEATURE:
```

```
<223> OTHER INFORMATION: Spacer sequence acquired by hCas9-expressing
      cells

<400> SEQUENCE: 54
taatacaggt ttttacaaaa gctttaccat                                          30

<210> SEQ ID NO 55
<211> LENGTH: 32
<212> TYPE: DNA
<213> ORGANISM: Artificial Sequence
<220> FEATURE:
<223> OTHER INFORMATION: Spacer sequence acquired by hCas9-expressing
      cells

<400> SEQUENCE: 55
tttttattta agtattcgat aatttcttta ta                                       32

<210> SEQ ID NO 56
<211> LENGTH: 31
<212> TYPE: DNA
<213> ORGANISM: Artificial Sequence
<220> FEATURE:
<223> OTHER INFORMATION: Spacer sequence acquired by hCas9-expressing
      cells

<400> SEQUENCE: 56
tgtatgtcgc tttgatacga tccatcaaca t                                        31

<210> SEQ ID NO 57
<211> LENGTH: 31
<212> TYPE: DNA
<213> ORGANISM: Artificial Sequence
<220> FEATURE:
<223> OTHER INFORMATION: Spacer sequence acquired by hCas9-expressing
      cells

<400> SEQUENCE: 57
attagacttt tactttccat tacttaaatc a                                        31

<210> SEQ ID NO 58
<211> LENGTH: 31
<212> TYPE: DNA
<213> ORGANISM: Artificial Sequence
<220> FEATURE:
<223> OTHER INFORMATION: Spacer sequence acquired by hCas9-expressing
      cells

<400> SEQUENCE: 58
attagacttt tactttccat tacttaaatc a                                        31

<210> SEQ ID NO 59
<211> LENGTH: 31
<212> TYPE: DNA
<213> ORGANISM: Artificial Sequence
<220> FEATURE:
<223> OTHER INFORMATION: Spacer sequence acquired by hCas9-expressing
      cells

<400> SEQUENCE: 59
ctaatactgt tttaattaag ttatcgatat c                                        31

<210> SEQ ID NO 60
<211> LENGTH: 30
<212> TYPE: DNA
<213> ORGANISM: Artificial Sequence
<220> FEATURE:
<223> OTHER INFORMATION: Spacer sequence acquired by hCas9-expressing
``` cells

<400> SEQUENCE: 60
atttatatcc gatcttatac gaagtaaaga                                              30

<210> SEQ ID NO 61
<211> LENGTH: 30
<212> TYPE: DNA
<213> ORGANISM: Artificial Sequence
<220> FEATURE:
<223> OTHER INFORMATION: Spacer sequence acquired by hCas9-expressing
      cells

<400> SEQUENCE: 61
gcaaagttga gcgatcagtc tgatttgatg                                              30

<210> SEQ ID NO 62
<211> LENGTH: 30
<212> TYPE: DNA
<213> ORGANISM: Artificial Sequence
<220> FEATURE:
<223> OTHER INFORMATION: Spacer sequence acquired by hCas9-expressing
      cells

<400> SEQUENCE: 62
ggaatatgat agcaattcaa ttgcacagta                                              30

<210> SEQ ID NO 63
<211> LENGTH: 30
<212> TYPE: DNA
<213> ORGANISM: Artificial Sequence
<220> FEATURE:
<223> OTHER INFORMATION: Spacer sequence acquired by hCas9-expressing
      cells

<400> SEQUENCE: 63
aaaatgcaag aattaaacta cccaccatat                                              30

<210> SEQ ID NO 64
<211> LENGTH: 31
<212> TYPE: DNA
<213> ORGANISM: Artificial Sequence
<220> FEATURE:
<223> OTHER INFORMATION: Spacer sequence acquired by hCas9-expressing
      cells

<400> SEQUENCE: 64
gataaaatca aacaacttca cgacgcaata a                                            31

<210> SEQ ID NO 65
<211> LENGTH: 31
<212> TYPE: DNA
<213> ORGANISM: Artificial Sequence
<220> FEATURE:
<223> OTHER INFORMATION: Spacer sequence acquired by hCas9-expressing
      cells

<400> SEQUENCE: 65
gataaaatca aacaacttca cgacgcaata a                                            31

<210> SEQ ID NO 66
<211> LENGTH: 30
<212> TYPE: DNA
<213> ORGANISM: Artificial Sequence
<220> FEATURE:
<223> OTHER INFORMATION: Spacer sequence acquired by hCas9-expressing
      cells

```
<400> SEQUENCE: 66
cgagtccaac acgtcatcaa attctttat                                        30

<210> SEQ ID NO 67
<211> LENGTH: 30
<212> TYPE: DNA
<213> ORGANISM: Artificial Sequence
<220> FEATURE:
<223> OTHER INFORMATION: Spacer sequence acquired by hCas9-expressing
      cells

<400> SEQUENCE: 67
atatacacac atactaaacc tgaacgatta                                       30

<210> SEQ ID NO 68
<211> LENGTH: 31
<212> TYPE: DNA
<213> ORGANISM: Artificial Sequence
<220> FEATURE:
<223> OTHER INFORMATION: Spacer sequence acquired by hCas9-expressing
      cells

<400> SEQUENCE: 68
tatgtgactc tattagagcc tcaatatgct t                                     31

<210> SEQ ID NO 69
<211> LENGTH: 33
<212> TYPE: DNA
<213> ORGANISM: Artificial Sequence
<220> FEATURE:
<223> OTHER INFORMATION: Spacer sequence acquired by hCas9-expressing
      cells

<400> SEQUENCE: 69
taagaatata gatccctata atgttatttt tgt                                   33

<210> SEQ ID NO 70
<211> LENGTH: 30
<212> TYPE: DNA
<213> ORGANISM: Artificial Sequence
<220> FEATURE:
<223> OTHER INFORMATION: Spacer sequence acquired by hCas9-expressing
      cells

<400> SEQUENCE: 70
gaatatagat ccctataatg ttattttgt                                        30

<210> SEQ ID NO 71
<211> LENGTH: 30
<212> TYPE: DNA
<213> ORGANISM: Artificial Sequence
<220> FEATURE:
<223> OTHER INFORMATION: Spacer sequence acquired by hCas9-expressing
      cells

<400> SEQUENCE: 71
ctcatcaata tcattctgat tggttatttt                                       30

<210> SEQ ID NO 72
<211> LENGTH: 30
<212> TYPE: DNA
<213> ORGANISM: Artificial Sequence
<220> FEATURE:
<223> OTHER INFORMATION: Spacer sequence acquired by hCas9-expressing
      cells
```

<400> SEQUENCE: 72
attgaaaaag atacgtatgc acattacaca                                30

<210> SEQ ID NO 73
<211> LENGTH: 31
<212> TYPE: DNA
<213> ORGANISM: Artificial Sequence
<220> FEATURE:
<223> OTHER INFORMATION: Spacer sequence acquired by hCas9-expressing
      cells

<400> SEQUENCE: 73
ctaagatagc taaagcaata cgtgatgatg t                               31

<210> SEQ ID NO 74
<211> LENGTH: 30
<212> TYPE: DNA
<213> ORGANISM: Artificial Sequence
<220> FEATURE:
<223> OTHER INFORMATION: Spacer sequence acquired by hCas9-expressing
      cells

<400> SEQUENCE: 74
gaacacgtga tactcatcgt catttagatg                                 30

<210> SEQ ID NO 75
<211> LENGTH: 31
<212> TYPE: DNA
<213> ORGANISM: Artificial Sequence
<220> FEATURE:
<223> OTHER INFORMATION: Spacer sequence acquired by hCas9-expressing
      cells

<400> SEQUENCE: 75
ctaatccttt cgaatgataa cgatctaatt c                               31

<210> SEQ ID NO 76
<211> LENGTH: 31
<212> TYPE: DNA
<213> ORGANISM: Artificial Sequence
<220> FEATURE:
<223> OTHER INFORMATION: Spacer sequence acquired by hCas9-expressing
      cells

<400> SEQUENCE: 76
tttgatgaaa ttttagttgt tcagatgtag t                               31

<210> SEQ ID NO 77
<211> LENGTH: 30
<212> TYPE: DNA
<213> ORGANISM: Artificial Sequence
<220> FEATURE:
<223> OTHER INFORMATION: Spacer sequence acquired by hCas9-expressing
      cells

<400> SEQUENCE: 77
taaactacta cgacttaagc aggtgccata                                 30

<210> SEQ ID NO 78
<211> LENGTH: 30
<212> TYPE: DNA
<213> ORGANISM: Artificial Sequence
<220> FEATURE:
<223> OTHER INFORMATION: Spacer sequence acquired by hCas9-expressing
      cells

<400> SEQUENCE: 78

```
taaactacta cgacttaagc aggtgccata                                    30

<210> SEQ ID NO 79
<211> LENGTH: 30
<212> TYPE: DNA
<213> ORGANISM: Artificial Sequence
<220> FEATURE:
<223> OTHER INFORMATION: Spacer sequence acquired by hCas9-expressing
      cells

<400> SEQUENCE: 79
aaaaataagg caactgacag ctagatattt                                    30

<210> SEQ ID NO 80
<211> LENGTH: 31
<212> TYPE: DNA
<213> ORGANISM: Artificial Sequence
<220> FEATURE:
<223> OTHER INFORMATION: Spacer sequence acquired by hCas9-expressing
      cells

<400> SEQUENCE: 80
tccattttgc tgttgattct tctatgctat c                                  31

<210> SEQ ID NO 81
<211> LENGTH: 30
<212> TYPE: DNA
<213> ORGANISM: Artificial Sequence
<220> FEATURE:
<223> OTHER INFORMATION: Spacer sequence acquired by hCas9-expressing
      cells

<400> SEQUENCE: 81
cctacgaata tgaacgacac aaatgattta                                    30

<210> SEQ ID NO 82
<211> LENGTH: 36
<212> TYPE: DNA
<213> ORGANISM: Artificial Sequence
<220> FEATURE:
<223> OTHER INFORMATION: Primer

<400> SEQUENCE: 82
aaacaaaaac aaaaatgttt taacacctat taacgg                             36

<210> SEQ ID NO 83
<211> LENGTH: 36
<212> TYPE: DNA
<213> ORGANISM: Artificial Sequence
<220> FEATURE:
<223> OTHER INFORMATION: Primer

<400> SEQUENCE: 83
aaaaccgtta ataggtgtta aaacattttt gttttt                             36

<210> SEQ ID NO 84
<211> LENGTH: 36
<212> TYPE: DNA
<213> ORGANISM: Artificial Sequence
<220> FEATURE:
<223> OTHER INFORMATION: Primer

<400> SEQUENCE: 84
aaacaaaaat gttttaacac ctattaacgt agtatg                             36
```

<210> SEQ ID NO 85
<211> LENGTH: 36
<212> TYPE: DNA
<213> ORGANISM: Artificial Sequence
<220> FEATURE:
<223> OTHER INFORMATION: Primer

<400> SEQUENCE: 85
aaaacatact acgttaatag gtgttaaaac attttt                    36

<210> SEQ ID NO 86
<211> LENGTH: 35
<212> TYPE: DNA
<213> ORGANISM: Artificial Sequence
<220> FEATURE:
<223> OTHER INFORMATION: Primer

<400> SEQUENCE: 86
aaaacaaaaa gcgcaagaag aaatcaacca gcgca                     35

<210> SEQ ID NO 87
<211> LENGTH: 35
<212> TYPE: DNA
<213> ORGANISM: Artificial Sequence
<220> FEATURE:
<223> OTHER INFORMATION: Primer

<400> SEQUENCE: 87 aaaactttt tacaaattga gttatgttca tataa                      35

<210> SEQ ID NO 88
<211> LENGTH: 32
<212> TYPE: DNA
<213> ORGANISM: Artificial Sequence
<220> FEATURE:
<223> OTHER INFORMATION: Primer

<400> SEQUENCE: 88
gctattttga gaggacaaga agacttttat cc                        32

<210> SEQ ID NO 89
<211> LENGTH: 32
<212> TYPE: DNA
<213> ORGANISM: Artificial Sequence
<220> FEATURE:
<223> OTHER INFORMATION: Primer

<400> SEQUENCE: 89
ggataaaagt cttcttgtcc tctcaaaata gc                        32

<210> SEQ ID NO 90
<211> LENGTH: 29
<212> TYPE: DNA
<213> ORGANISM: Artificial Sequence
<220> FEATURE:
<223> OTHER INFORMATION: Primer

<400> SEQUENCE: 90
ggaagtctga agaaacattt accccatgg                            29

<210> SEQ ID NO 91
<211> LENGTH: 29
<212> TYPE: DNA
<213> ORGANISM: Artificial Sequence
<220> FEATURE:
<223> OTHER INFORMATION: Primer

<400> SEQUENCE: 91
ccatggggta aatgtttctt cagacttcc            29

<210> SEQ ID NO 92
<211> LENGTH: 42
<212> TYPE: DNA
<213> ORGANISM: Artificial Sequence
<220> FEATURE:
<223> OTHER INFORMATION: Primer

<400> SEQUENCE: 92
gacaaacttt gatataaatc ttccaaatga aaagtacta cc            42

<210> SEQ ID NO 93
<211> LENGTH: 42
<212> TYPE: DNA
<213> ORGANISM: Artificial Sequence
<220> FEATURE:
<223> OTHER INFORMATION: Primer

<400> SEQUENCE: 93
ggtagtactt tttcatttgg aagatttata tcaaagtttg tc            42

<210> SEQ ID NO 94
<211> LENGTH: 31
<212> TYPE: DNA
<213> ORGANISM: Artificial Sequence
<220> FEATURE:
<223> OTHER INFORMATION: Primer

<400> SEQUENCE: 94
ccatgatgat ggtttgacat ttaaagaaga c            31

<210> SEQ ID NO 95
<211> LENGTH: 31
<212> TYPE: DNA
<213> ORGANISM: Artificial Sequence
<220> FEATURE:
<223> OTHER INFORMATION: Primer

<400> SEQUENCE: 95
gtcttcttta aatgtcaaac catcatcatg g            31

<210> SEQ ID NO 96
<211> LENGTH: 25
<212> TYPE: DNA
<213> ORGANISM: Artificial Sequence
<220> FEATURE:
<223> OTHER INFORMATION: Primer

<400> SEQUENCE: 96
gggcggcata agctagaaaa tatcg            25

<210> SEQ ID NO 97
<211> LENGTH: 25
<212> TYPE: DNA
<213> ORGANISM: Artificial Sequence
<220> FEATURE:
<223> OTHER INFORMATION: Primer

<400> SEQUENCE: 97
cgatattttc tagcttatgc cgccc            25

<210> SEQ ID NO 98
<211> LENGTH: 24

```
<212> TYPE: DNA
<213> ORGANISM: Artificial Sequence
<220> FEATURE:
<223> OTHER INFORMATION: Primer

<400> SEQUENCE: 98
gcaagaaata ggcaaaggaa ccgc                                       24

<210> SEQ ID NO 99
<211> LENGTH: 24
<212> TYPE: DNA
<213> ORGANISM: Artificial Sequence
<220> FEATURE:
<223> OTHER INFORMATION: Primer

<400> SEQUENCE: 99
gcggttcctt tgcctatttc ttgc                                       24

<210> SEQ ID NO 100
<211> LENGTH: 29
<212> TYPE: DNA
<213> ORGANISM: Artificial Sequence
<220> FEATURE:
<223> OTHER INFORMATION: Primer

<400> SEQUENCE: 100
ggaagtctga agaaacagct accccatgg                                  29

<210> SEQ ID NO 101
<211> LENGTH: 29
<212> TYPE: DNA
<213> ORGANISM: Artificial Sequence
<220> FEATURE:
<223> OTHER INFORMATION: Primer

<400> SEQUENCE: 101
ccatggggta gctgtttctt cagacttcc                                  29

<210> SEQ ID NO 102
<211> LENGTH: 30
<212> TYPE: DNA
<213> ORGANISM: Artificial Sequence
<220> FEATURE:
<223> OTHER INFORMATION: Primer

<400> SEQUENCE: 102
gcaaaaatgg ataagaaata ctcaataggc                                 30

<210> SEQ ID NO 103
<211> LENGTH: 31
<212> TYPE: DNA
<213> ORGANISM: Artificial Sequence
<220> FEATURE:
<223> OTHER INFORMATION: Primer

<400> SEQUENCE: 103
tattgagtat ttcttatcca tttttgcctc c                               31

<210> SEQ ID NO 104
<211> LENGTH: 23
<212> TYPE: DNA
<213> ORGANISM: Artificial Sequence
<220> FEATURE:
<223> OTHER INFORMATION: Primer

<400> SEQUENCE: 104
```

```
aacacgcatt gatttgagtc agc                                              23

<210> SEQ ID NO 105
<211> LENGTH: 24
<212> TYPE: DNA
<213> ORGANISM: Artificial Sequence
<220> FEATURE:
<223> OTHER INFORMATION: Primer

<400> SEQUENCE: 105
tcctagctga ctcaaatcaa tgcg                                             24

<210> SEQ ID NO 106
<211> LENGTH: 26
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(5)
<223> OTHER INFORMATION: n is a, c, g, or t

<400> SEQUENCE: 106
nnnnnactag gggcttttca agactg                                           26

<210> SEQ ID NO 107
<211> LENGTH: 26
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(5)
<223> OTHER INFORMATION: n is a, c, g, or t

<400> SEQUENCE: 107
nnnnnactga agaaatcaac cagcgc                                           26

<210> SEQ ID NO 108
<211> LENGTH: 26
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(5)
<223> OTHER INFORMATION: n is a, c, g, or t

<400> SEQUENCE: 108
nnnnnctgag gggcttttca agactg                                           26

<210> SEQ ID NO 109
<211> LENGTH: 26
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(5)
<223> OTHER INFORMATION: n is a, c, g, or t

<400> SEQUENCE: 109
nnnnnctgga agaaatcaac cagcgc                                           26
```

```
<210> SEQ ID NO 110
<211> LENGTH: 26
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(5)
<223> OTHER INFORMATION: n is a, c, g, or t

<400> SEQUENCE: 110
nnnnntgaag gggctttcta agactg                                          26

<210> SEQ ID NO 111
<211> LENGTH: 26
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(5)
<223> OTHER INFORMATION: n is a, c, g, or t

<400> SEQUENCE: 111
nnnnntgaga agaaatcaac cagcgc                                          26

<210> SEQ ID NO 112
<211> LENGTH: 44
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (20)..(29)
<223> OTHER INFORMATION: n is a, c, g, or t

<400> SEQUENCE: 112 cagggggcttt tcaagactgn nnnnnnnnng agacaaatag tgcg                      44

<210> SEQ ID NO 113
<211> LENGTH: 19
<212> TYPE: DNA
<213> ORGANISM: Artificial Sequence
<220> FEATURE:
<223> OTHER INFORMATION: Primer

<400> SEQUENCE: 113
cagtcttgaa aagcccctg                                                  19

<210> SEQ ID NO 114
<211> LENGTH: 35
<212> TYPE: DNA
<213> ORGANISM: Artificial Sequence
<220> FEATURE:
<223> OTHER INFORMATION: Primer

<400> SEQUENCE: 114
aaactgaata ttcatctctc ggtatatata atccg                                35

<210> SEQ ID NO 115
<211> LENGTH: 35
<212> TYPE: DNA
<213> ORGANISM: Artificial Sequence
<220> FEATURE:
<223> OTHER INFORMATION: Primer
```

<400> SEQUENCE: 115
aaaacggatt atatataccg agagatgaat attca                               35

<210> SEQ ID NO 116
<211> LENGTH: 35
<212> TYPE: DNA
<213> ORGANISM: Artificial Sequence
<220> FEATURE:
<223> OTHER INFORMATION: Primer

<400> SEQUENCE: 116
aaacccagaa gttatgatag ctaattcgtc atcag                               35

<210> SEQ ID NO 117
<211> LENGTH: 35
<212> TYPE: DNA
<213> ORGANISM: Artificial Sequence
<220> FEATURE:
<223> OTHER INFORMATION: Primer

<400> SEQUENCE: 117
aaaactgatg acgaattagc tatcataact tctgg                               35

<210> SEQ ID NO 118
<211> LENGTH: 35
<212> TYPE: DNA
<213> ORGANISM: Artificial Sequence
<220> FEATURE:
<223> OTHER INFORMATION: Primer

<400> SEQUENCE: 118
aaacatgctc caatcgataa acaattagat aaacg                               35

<210> SEQ ID NO 119
<211> LENGTH: 35
<212> TYPE: DNA
<213> ORGANISM: Artificial Sequence
<220> FEATURE:
<223> OTHER INFORMATION: Primer

<400> SEQUENCE: 119
aaaacgttta tctaattgtt tatcgattgg agcat                               35

<210> SEQ ID NO 120
<211> LENGTH: 25
<212> TYPE: DNA
<213> ORGANISM: Artificial Sequence
<220> FEATURE:
<223> OTHER INFORMATION: Primer

<400> SEQUENCE: 120
cgaaattttt tagacaaaaa tagtc                                          25

<210> SEQ ID NO 121
<211> LENGTH: 55
<212> TYPE: DNA
<213> ORGANISM: Artificial Sequence
<220> FEATURE:
<223> OTHER INFORMATION: Primer

<400> SEQUENCE: 121
gagtggaagg atgccagtga taagtggaat gccatgtggg ctgtcaaaat tgagc         55

<210> SEQ ID NO 122
<211> LENGTH: 55

```
<212> TYPE: DNA
<213> ORGANISM: Artificial Sequence
<220> FEATURE:
<223> OTHER INFORMATION: Primer

<400> SEQUENCE: 122
gctcaatttt gacagcccac atggcattcc acttatcact ggcatccttc cactc      55

<210> SEQ ID NO 123
<211> LENGTH: 55
<212> TYPE: DNA
<213> ORGANISM: Artificial Sequence
<220> FEATURE:
<223> OTHER INFORMATION: Primer

<400> SEQUENCE: 123
gagtggaagg atgccagtga taagtggaat gccatgtagg ctgtcaaaat tgagc      55

<210> SEQ ID NO 124
<211> LENGTH: 55
<212> TYPE: DNA
<213> ORGANISM: Artificial Sequence
<220> FEATURE:
<223> OTHER INFORMATION: Primer

<400> SEQUENCE: 124
gctcaatttt gacagcctac atggcattcc acttatcact ggcatccttc cactc      55

<210> SEQ ID NO 125
<211> LENGTH: 42
<212> TYPE: RNA
<213> ORGANISM: Artificial Sequence
<220> FEATURE:
<223> OTHER INFORMATION: crRNA

<400> SEQUENCE: 125
gugauaagug gaaugccaug guuuuagagc uaugcuguuu ug                    42

<210> SEQ ID NO 126
<211> LENGTH: 73
<212> TYPE: RNA
<213> ORGANISM: Artificial Sequence
<220> FEATURE:
<223> OTHER INFORMATION: tracrRNA

<400> SEQUENCE: 126
ggacagcaua gcaaguuaaa auaaggcuag uccguuauca acuugaaaaa guggcaccga  60
gucggugcuu uuu                                                    73

<210> SEQ ID NO 127
<211> LENGTH: 128
<212> TYPE: RNA
<213> ORGANISM: Artificial Sequence
<220> FEATURE:
<223> OTHER INFORMATION: sgRNA

<400> SEQUENCE: 127
gacgcauaaa gaugagacgc guuuuagagc uaugcuguuu uggaaacaaa acagcauagc  60
aaguuaaaau aaggcuaguc cguuaucaac uugaaaagu ggcaccgagu cggugcuuuu  120
uuuggauc                                                          128

<210> SEQ ID NO 128
<211> LENGTH: 52
<212> TYPE: DNA
```

```
<213> ORGANISM: Artificial Sequence
<220> FEATURE:
<223> OTHER INFORMATION: Protospacer

<400> SEQUENCE: 128
tagataaaaa caaaaatgtt ttaacaccta ttaacgtagt attggaatct ga          52

<210> SEQ ID NO 129
<211> LENGTH: 52
<212> TYPE: DNA
<213> ORGANISM: Artificial Sequence
<220> FEATURE:
<223> OTHER INFORMATION: Protospacer

<400> SEQUENCE: 129
tgaatattca tctctcggta tatataatcc aagttatttg catgctccaa tc          52

<210> SEQ ID NO 130
<211> LENGTH: 52
<212> TYPE: DNA
<213> ORGANISM: Artificial Sequence
<220> FEATURE:
<223> OTHER INFORMATION: Protospacer

<400> SEQUENCE: 130
gataaacaat tagataaacc agaagttatg atagctaatt cgtcatcaga gt          52

<210> SEQ ID NO 131
<211> LENGTH: 50
<212> TYPE: DNA
<213> ORGANISM: Artificial Sequence
<220> FEATURE:
<223> OTHER INFORMATION: Protospacer

<400> SEQUENCE: 131
tagataaaaa caaaaatgtt ttaacaccta ttaacgtagt attggaatct             50

<210> SEQ ID NO 132
<211> LENGTH: 55
<212> TYPE: DNA
<213> ORGANISM: Artificial Sequence
<220> FEATURE:
<223> OTHER INFORMATION: Protospacer

<400> SEQUENCE: 132
gagtggaagg atgccagtga taagtgcaat gccatgtggg ctgtcaaaat tgagc       55

<210> SEQ ID NO 133
<211> LENGTH: 55
<212> TYPE: DNA
<213> ORGANISM: Artificial Sequence
<220> FEATURE:
<223> OTHER INFORMATION: Protospacer

<400> SEQUENCE: 133
gctcaatttt gacagcccac atggcattcc acttatcact ggcatccttc cactc       55

<210> SEQ ID NO 134
<211> LENGTH: 55
<212> TYPE: DNA
<213> ORGANISM: Artificial Sequence
<220> FEATURE:
<223> OTHER INFORMATION: Protospacer

<400> SEQUENCE: 134
gagtggaagg atgccagtga taagtggaat gccatgtagg ctgtcaaaat tgagc       55
```

<210> SEQ ID NO 135
<211> LENGTH: 55
<212> TYPE: DNA
<213> ORGANISM: Artificial Sequence
<220> FEATURE:
<223> OTHER INFORMATION: Protospacer

<400> SEQUENCE: 135
gctcaatttt gacagcctac atggcattcc acttatcact ggcatccttc cactc          55

<210> SEQ ID NO 136
<211> LENGTH: 23
<212> TYPE: PRT
<213> ORGANISM: Francisella novicida

<400> SEQUENCE: 136

Tyr Lys Asp Leu Asp Ala Arg Ile Leu Gln Phe Ile Phe Asp Arg Val
1               5                   10                  15

Lys Ala Ser Asp Glu Leu Leu
            20

<210> SEQ ID NO 137
<211> LENGTH: 6
<212> TYPE: PRT
<213> ORGANISM: Prevotellamassilia timonensis

<400> SEQUENCE: 137

Lys Ser Gln Arg His Gly
1               5

<210> SEQ ID NO 138
<211> LENGTH: 29
<212> TYPE: PRT
<213> ORGANISM: Streptococcus thermophious(3)

<400> SEQUENCE: 138

Arg Lys Arg Asn Glu Lys Ile Thr Pro Trp Asn Phe Glu Asp Val Ile
1               5                   10                  15

Asp Lys Glu Ser Ser Ala Glu Ala Phe Ile Asn Arg Met
            20                  25

<210> SEQ ID NO 139
<211> LENGTH: 29
<212> TYPE: PRT
<213> ORGANISM: Streptococcus pyogenes

<400> SEQUENCE: 139

Arg Lys Ser Glu Glu Thr Ile Thr Pro Trp Asn Phe Glu Glu Val Val
1               5                   10                  15

Asp Lys Gly Ala Ser Ala Gln Ser Phe Ile Glu Arg Met
            20                  25

<210> SEQ ID NO 140
<211> LENGTH: 29
<212> TYPE: PRT
<213> ORGANISM: Streptococcus mutans

<400> SEQUENCE: 140

Arg Lys Ser Ala Asp Lys Ile Thr Pro Trp Asn Phe Asp Glu Ile Val
1               5                   10                  15

Asp Lys Glu Ser Ser Ala Glu Ala Phe Ile Asn Arg Met
            20                  25

<210> SEQ ID NO 141
<211> LENGTH: 29
<212> TYPE: PRT
<213> ORGANISM: Lactobacillus farciminis

<400> SEQUENCE: 141

Arg Lys Ser Asn Gly His Ala Arg Pro Trp Asn Phe Asp Glu Ile Val
1               5                   10                  15

Asp Arg Glu Lys Ser Ser Asn Lys Phe Ile Arg Arg Met
            20                  25

<210> SEQ ID NO 142
<211> LENGTH: 30
<212> TYPE: PRT
<213> ORGANISM: Catenibacterium mitsuokai

<400> SEQUENCE: 142

Glu Gly Lys Glu Asn Gln Arg Ile Leu Pro Trp Asn Tyr Gln Asp Ile
1               5                   10                  15

Val Asp Val Asp Ala Thr Ala Glu Gly Phe Ile Lys Arg Met
            20                  25                  30

<210> SEQ ID NO 143
<211> LENGTH: 30
<212> TYPE: PRT
<213> ORGANISM: Coriobacterium glomerans

<400> SEQUENCE: 143

Pro Gly Met Gln Asp Glu Pro Ile Phe Pro Trp Asn Trp Glu Ser Ile
1               5                   10                  15

Ile Asp Arg Ser Lys Ser Ala Glu Lys Phe Ile Leu Arg Met
            20                  25                  30

<210> SEQ ID NO 144
<211> LENGTH: 27
<212> TYPE: PRT
<213> ORGANISM: Veillonella atypica

<400> SEQUENCE: 144

Gln Ala Gly Arg Val Thr Pro Trp Asn Phe Glu Glu Lys Ile Asp Arg
1               5                   10                  15

Glu Lys Ser Ala Ala Ala Phe Ile Lys Asn Leu
            20                  25

<210> SEQ ID NO 145
<211> LENGTH: 30
<212> TYPE: PRT
<213> ORGANISM: Treponema denticola

<400> SEQUENCE: 145

Glu Lys Ser Pro Ser Gly Lys Thr Thr Pro Trp Asn Phe Phe Asp His
1               5                   10                  15

Ile Asp Lys Asp Lys Thr Ala Glu Ala Phe Ile Thr Ser Arg
            20                  25                  30

<210> SEQ ID NO 146
<211> LENGTH: 29
<212> TYPE: PRT
<213> ORGANISM: Filifactor alocis

<400> SEQUENCE: 146

-continued

Pro Gly Arg Glu Asp Arg Ile Tyr Pro Trp Asn Met Glu Glu Ile Ile
1               5                   10                  15

Asp Phe Glu Lys Ser Asn Glu Asn Phe Ile Thr Arg Met
            20                  25

<210> SEQ ID NO 147
<211> LENGTH: 28
<212> TYPE: PRT
<213> ORGANISM: Lactobacillus rhamnosus

<400> SEQUENCE: 147

Asp Pro Ser Gly Asn Ile Thr Pro Tyr Asn Phe Asp Glu Lys Val Asp
1               5                   10                  15

Arg Glu Ala Ser Ala Asn Thr Phe Ile Gln Arg Met
            20                  25

<210> SEQ ID NO 148
<211> LENGTH: 30
<212> TYPE: PRT
<213> ORGANISM: Fructobacillus fructosus

<400> SEQUENCE: 148

Glu Gly Phe Glu Lys Ser Arg Val Thr Pro Trp Asn Phe Asp Lys Val
1               5                   10                  15

Phe Asn Arg Asp Lys Ala Ala Arg Asp Phe Ile Glu Arg Leu
            20                  25                  30

<210> SEQ ID NO 149
<211> LENGTH: 27
<212> TYPE: PRT
<213> ORGANISM: Bifidobacterium bifidum

<400> SEQUENCE: 149

Lys Lys Gly Glu Ile Thr Pro Trp Asn Phe Asp Glu Met Val Asp Lys
1               5                   10                  15

Asp Ala Ser Gly Arg Lys Phe Ile Glu Arg Leu
            20                  25

<210> SEQ ID NO 150
<211> LENGTH: 4
<212> TYPE: PRT
<213> ORGANISM: Nitrobacter hamburgensis

<400> SEQUENCE: 150

Lys Pro Ala Ile
1

<210> SEQ ID NO 151
<211> LENGTH: 16
<212> TYPE: PRT
<213> ORGANISM: Microsporum canis

<400> SEQUENCE: 151

Gly Asp Asn Gly Gln Gly Gly Arg Tyr Glu His Ile Trp Asp Lys Asn
1               5                   10                  15

<210> SEQ ID NO 152
<211> LENGTH: 7
<212> TYPE: PRT
<213> ORGANISM: Campylobacter jejuni

<400> SEQUENCE: 152

Leu Lys Asp Phe Ser His Leu

```
<210> SEQ ID NO 153
<211> LENGTH: 9
<212> TYPE: PRT
<213> ORGANISM: Neisseria meningitidis

<400> SEQUENCE: 153

Leu Ser Gly Asp Ala Val Gln Lys Met
1               5

<210> SEQ ID NO 154
<211> LENGTH: 14
<212> TYPE: PRT
<213> ORGANISM: Streptococcus thermophilus(1)

<400> SEQUENCE: 154

Arg Thr Ser Gly Glu Thr Leu Asp Asn Ile Phe Gly Ile Leu
1               5                   10

<210> SEQ ID NO 155
<211> LENGTH: 9
<212> TYPE: PRT
<213> ORGANISM: Staphylococcus lugdunensis

<400> SEQUENCE: 155

Asp Pro Lys Ala Trp Tyr Glu Thr Leu
1               5
```

COMPOSITIONS AND METHODS USING CAS9 WITH ENHANCED SPACER ACQUISITION FUNCTION

CROSS REFERENCE TO RELATED APPLICATIONS

This application is a national phase application of PCT application no. PCT/US2017/06937, which claims priority to U.S. provisional application No. 62/435,406, filed Dec. 16, 2016, the disclosures of each of which are incorporated herein by reference.

SEQUENCE LISTING

The instant application contains a Sequence Listing which has been submitted electronically in ASCII format and is hereby incorporated by reference in its entirety. Said ASCII copy was created on Dec. 18, 2017, and is named "076091_00041_Sequence Listing ST25.txt" and is 42,300 bytes in size.

FIELD

The present disclosure relates generally to Clustered regularly interspaced short palindromic repeat (CRISPR) systems, and more particularly to compositions and methods involving an improved Cas9 nuclease with enhanced spacer acquisition properties.

BACKGROUND

Clustered regularly interspaced short palindromic repeat (CRISPR) loci and their associated (Cas) proteins protect bacteria and archaea against their viruses (Barrangou et al., 2007) and plasmids (Marraffini and Sontheimer, 2008). In the first step of the CRISPR immune response, a very low proportion of the infected cells acquire a short sequence, known as a spacer sequence, of the invading genome in between the repeats of the CRISPR array (Barrangou et al., 2007). Spacer acquisition is catalyzed by the Cas1/Cas2 integration complex (Nunez et al., 2014; Nunez et al., 2015; Yosef et al., 2012) and results in the immunization of the host (Barrangou et al., 2007). In the second step of the CRISPR immune response, spacer sequences are transcribed and processed into a small RNA known as the CRISPR RNA (crRNA) (Brouns et al., 2008; Carte et al., 2008; Deltcheva et al., 2011). The crRNA is used as a guide by Cas nucleases to find its complementary sequence, known as the protospacer, in the invading viral or plasmid genome (Gasiunas et al., 2012; Jinek et al., 2012; Jore et al., 2011; Samai et al., 2015). Target recognition through base-pairing between the crRNA and the target DNA results in the destruction of the invader and host immunity (Garneau et al., 2010).

Based on their cas genetic repertoire, CRISPR-Cas systems have been classified into six types, I through VI (Makarova et al., 2015; Shmakov et al., 2015). Cas9 is the crRNA-guided nuclease of the type II-A CRISPR-Cas system of *Streptococcus pyogenes* (Jinek et al., 2012). In addition to protospacer recognition by the crRNA, Cas9 target cleavage requires a 5'-NGG-3' protospacer adjacent motif (PAM) immediately downstream of the target (Anders et al., 2014; Deveau et al., 2008; Jiang et al., 2013; Jinek et al., 2012). Cas9 is also required for the immunization step of the CRISPR response (Heler et al., 2015; Wei et al., 2015), using its PAM binding domain to specify functional spacer sequences that are flanked by the required NGG motif (Heler et al., 2015). In support of its role in spacer acquisition, Cas9 can associate in vivo with the other proteins encoded by the type II-A CRISPR-Cas system: Cas1, Cas2 and Csn2 (Heler et al., 2015). Cas9 systems have been utilized in a wide variety of compositions and methods, but there is an ongoing and unmet need for improvements in such systems, and methods of using them. This disclosure is pertinent to these needs.

SUMMARY

The present disclosure relates to a novel Cas9 enzyme comprising mutations that enhance its properties, relative to un-mutated Cas9. In particular, the altered Cas9 enzymes of this disclosure exhibit i) an increased rate of spacer acquisition, or ii) increased cleavage efficiency of targets with NAG PAMs, or a combination of i) and ii). The altered Cas9 enzymes comprise an amino acid substitution of I473 and K500 in a *Streptococcus pyogenes* Cas9 enzyme, one non-limiting example of which is provided in SEQ ID NO:1 as a non-mutated sequence, but other homologous changes can be made in other Cas9 enzymes. Thus, in embodiments, novel Cas9 enzymes of this disclosure comprise sequences that are at least 80% similar to SEQ ID NO:1 across its length, but retain one or more of the increased rate of spacer acquisition, or increased cleavage efficiency.

The disclosure includes polynucleotides, including but not limited to expression vectors, that encode the Cas9 enzymes described herein, cells comprising such polynucleotides, and methods of using such cells for a variety of purposes, such as for use in labelling bacteria, and for enhancing phage acquired immunity in bacteria, such as those used in industrial processes, including but not necessarily limited to the food a beverage industry, such as the dairy industry.

The disclosure includes methods of making modified bacteria by introducing into them expression vectors that encode the novel Cas9 enzymes described herein, and includes the modified cells, their cell culture medium, cell lysates, and Cas9 enzymes isolated from the cells.

In one approach the disclosure provides a method comprising contacting bacteria that have been modified to express a Cas9 described herein with one or more bacteriophage such that at least one spacer sequence in the genome of the bacteriophage is acquired by the bacteria. Spacer acquisition is more efficient than compared to a reference, such as an unmodified Cas9, i.e., a Cas9 that does not contain the described mutations. In certain embodiments, the bacteria are contacted with a plurality of distinct bacteriophage, and the bacteria acquire a plurality of distinct spacer sequences. In such implementations, the bacteriophage can be obtained from any source, including but not limited to a bacterial culture that is used in connection with making or finishing a food or beverage product. Such food products made with the assistance of modified bacteria are included within this disclosure.

BRIEF DESCRIPTION OF FIGURES

Where color is described as a feature in the figures, arrows and text are also used to illustrate certain of those features.

The patent or application file contains at least one drawing executed in color. Copies of this patent or patent application publication with color drawing(s) will be provided by the Office upon request and payment of the necessary fee.

Schematic diagram of the directed evolution assay. *S. pyogenes* cas9 was mutagenized by error-prone PCR and library amplicons were cloned into a plasmid carrying a spacer matching a TAG-adjacent target sequence on the ϕNM4γ4 phage. Library cells were infected with lytic phage to screen for mutants displaying improved NAG cleaving efficiency. (B) Phage propagation was measured as the number of plaque forming units (pfu) per ml of stock, on cells targeting the NAG-adjacent protospacer and harboring plasmids with different mutations on cas9: one of the "evolved" alleles or each of the six mutations present in this allele. Mutations with pfu values significantly different than wild type are highlighted (**, p-value <0.05 compared to wtCas9). (C) Colony forming units (cfu) obtained after phage infection of naïve cells (not programmed to target any viral sequence) harboring plasmids with different mutations in cas9. Mutations with cfu values significantly different than wild type are highlighted. (D) Location of residues I473 and K500 on the Cas9:single-guide RNA ribonucleoprotein (PDB 4UN3). Red, I473; purple, K500; orange, sgRNA; green, target DNA (the GG PAM highlighted in red); grey, alpha-helical (REC) lobe; yellow, HNH domain; light blue, RuvC domain; blue, PAM-interacting CTD.

Figure 2:
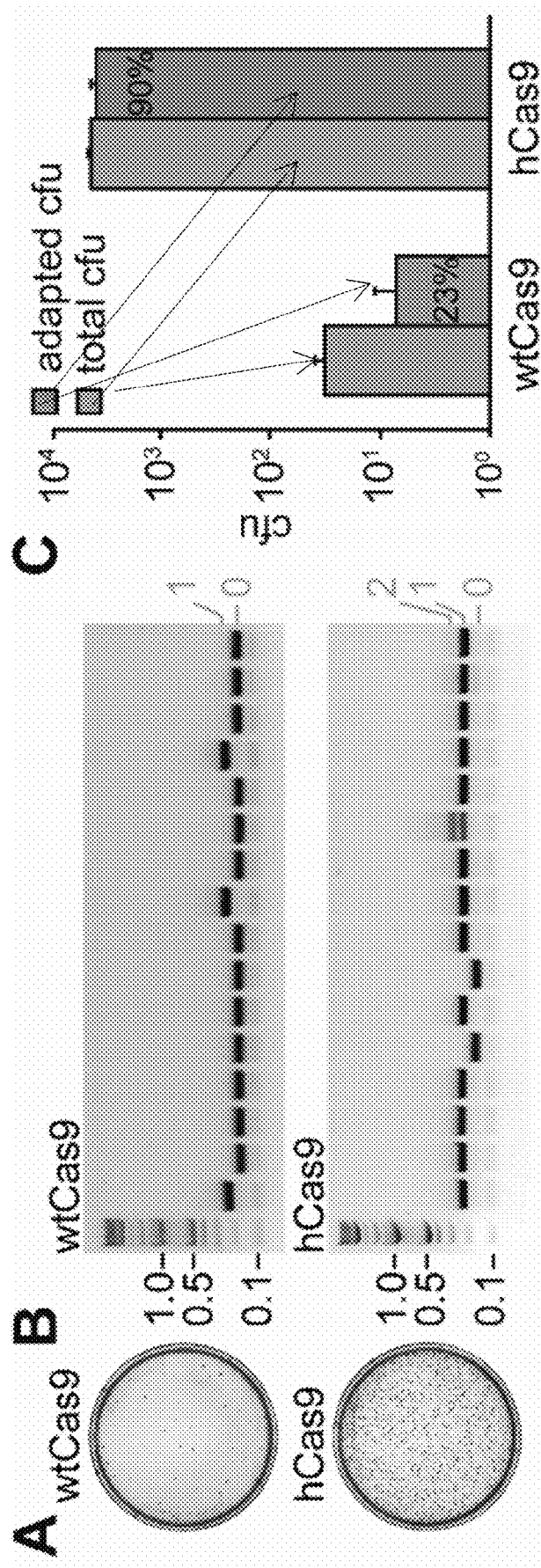
Figure 2:
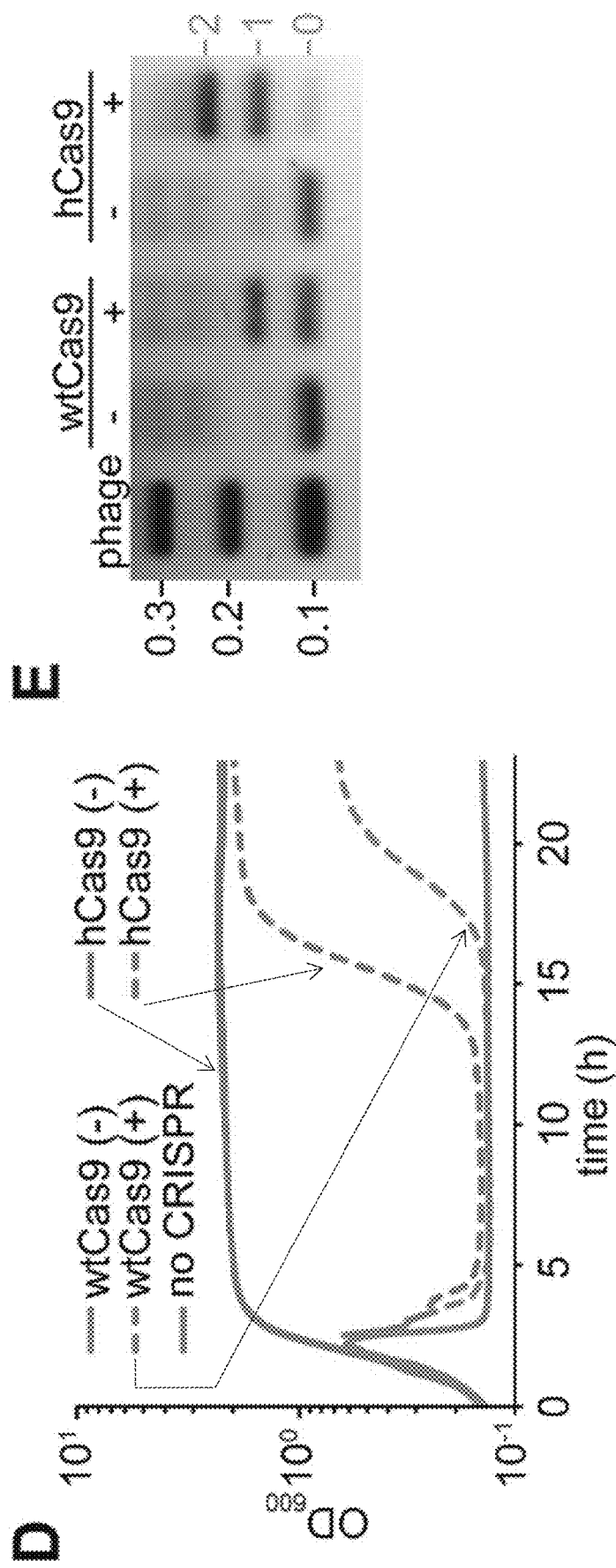

FIG. 2. Cas9$^{73'}$, or hyper-Cas9 (hCas9) mounts an enhanced CRISPR adaptive immune response. See also FIG. 6. (A) Representative plates obtained after lytic infection of cells harboring the full CRISPR system of *S. pyogenes* with wtCas9 or hCas9, showing the number of surviving colonies. (B) Agarose gel electrophoresis of PCR products of the amplification of the CRISPR of arrays of surviving cells to detect newly acquired spacers (asterisks). Molecular markers (in kb) are indicated in black, number of new spacers added in green. (C) Quantification of total surviving colonies (gray bars) and surviving colonies with newly incorporated spacers, as detected by PCR (blue and red bars). Data are represented as mean±SEM of 3 representative biological replicates. (B) Growth curves of cultures of cells harboring the full CRISPR system of *S. pyogenes* with wtCas9 or hCas9, with (+) or without (−) phage infection. (E) PCR-based analysis of the liquid cultures shown in C (at 24 hours post-infection) to check for the acquisition of new spacer sequences in the presence (+) or the absence (−) of phage ϕNM4γ4 infection, by cells expressing wtCas9 or hCas9. Molecular markers (in kb) are indicated in black, number of new spacers added in green. Image is representative of three technical replicates.

Figure 3:
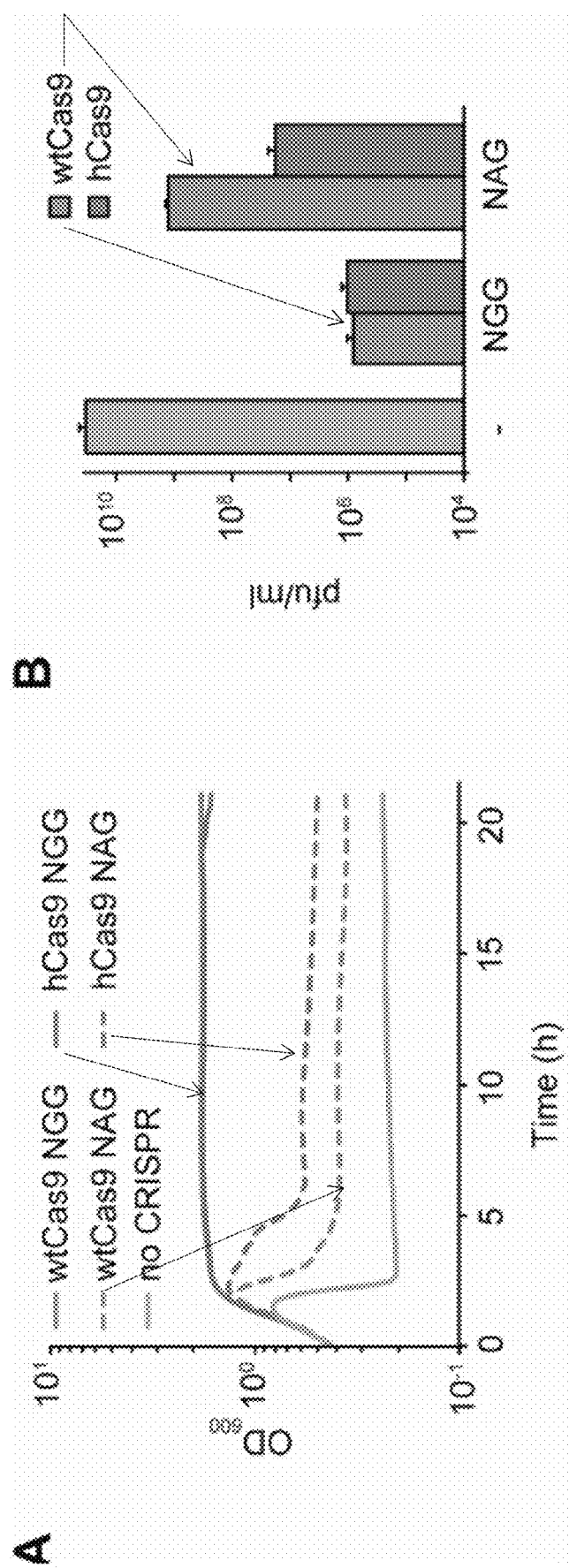
Figure 3:
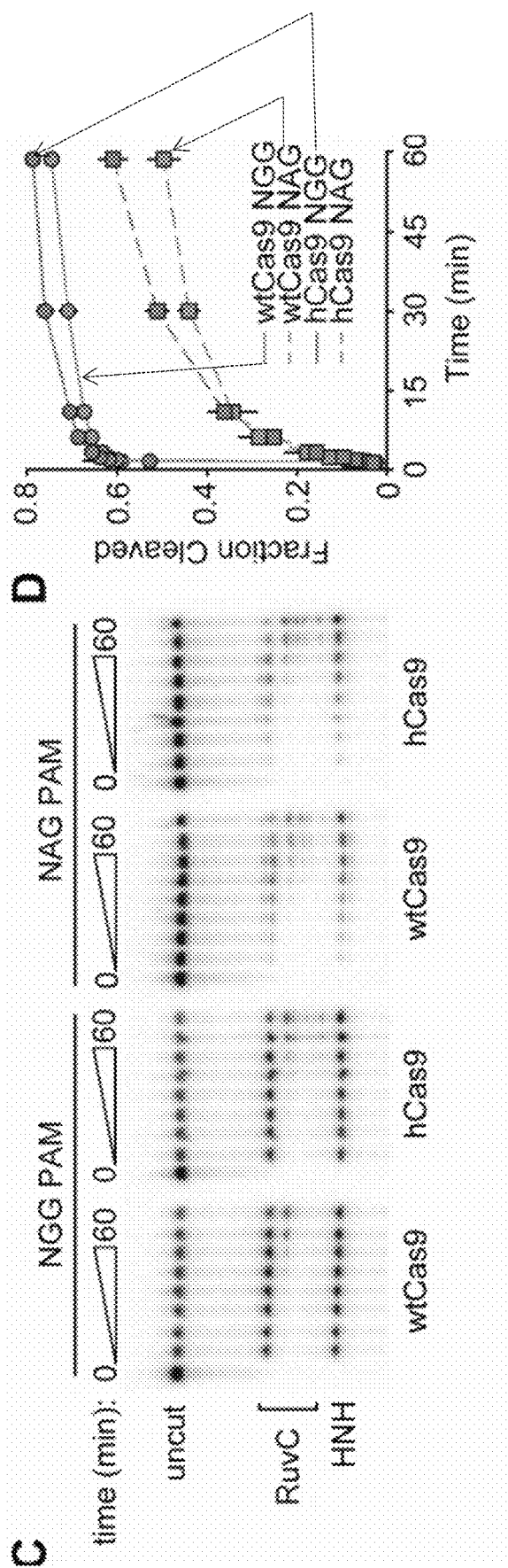

FIG. 3. hCas9 has increased interference efficiency against NAG- but not NGG-adjacent targets. See also FIG. 7. (A) Growth curves of cultures infected with ϕNM4γ4 harboring the wtCas9 or hCas9 (but not Cas1, Cas2 and Csn2) programmed to target either NAG- or NGG-flanked viral sequences. (B) Phage propagation, measured in pfu/ml, of the bacteria presented in A. (C) Cleavage of radiolabeled dsDNA targets flanked by either NGG or NAG PAMs, by wtCas9 or hCas9. (D) Quantification of the cleavage results shown in C. Data are represented as mean SD of 3 representative biological replicates.

Figure 4:
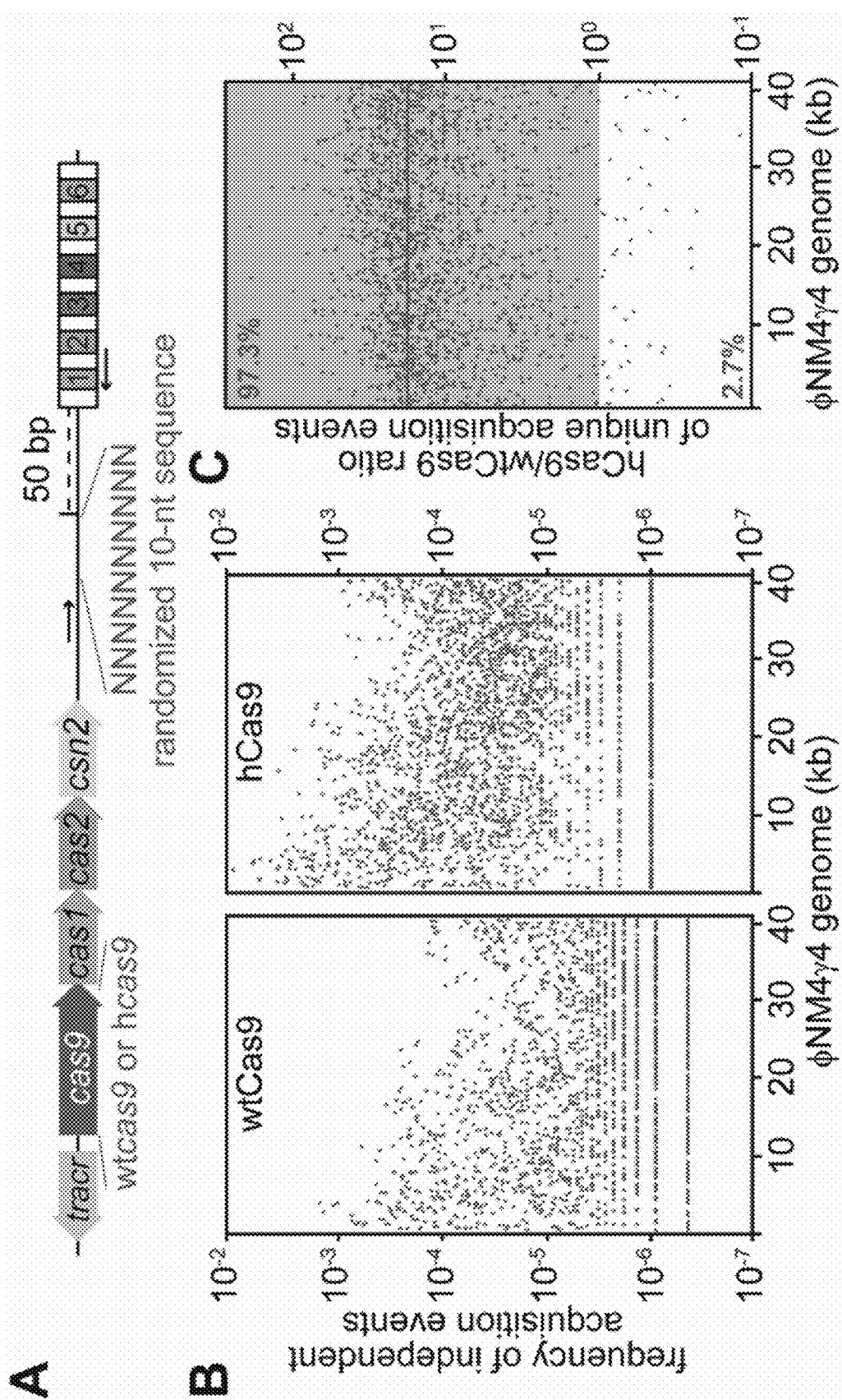
Figure 4:
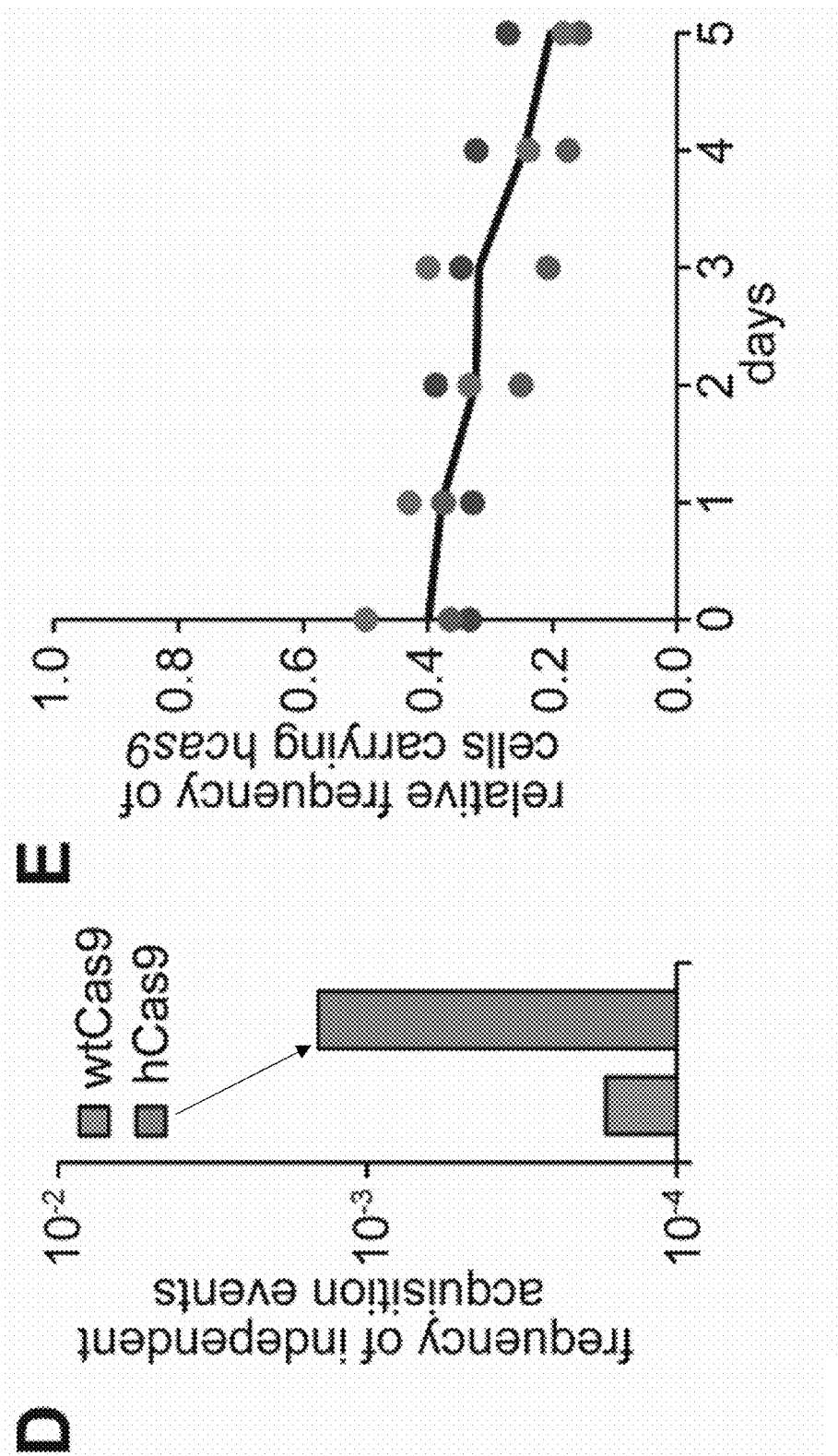

FIG. 4. hCas9 promotes higher rates of spacer acquisition. See also FIG. 8. (A) Schematic diagram of the *S. pyogenes* CRISPR locus showing the barcode and primers (arrows) used to measure the number of independent spacer acquisition events. (B) Cultures expressing wtCas9 or hCas9 were infected with ϕNM4γ4 phage, surviving cells were collected after 24 hours, DNA extracted and used as template for PCR of the CRISPR arrays. Amplification products were separated by agarose gel electrophoresis (not shown) and the DNA of the expanded CRISPR array was subject to MiSeq next-generation sequencing. The number of barcodes for each spacer sequence across the phage genome, normalized by the total number of spacer reads obtained, was plotted. (C) The hCas9/wtCas9 frequency of independent acquisition events ratio for 1938 common spacer sequences was plotted across the phage genome. The zone where the ratio is greater than one is shown in grey. The red line shows the average ratio. (D) Same as (B) but without phage infection; i.e. a measure of acquisition of spacers derived from the host chromosome and resident plasmids. (E) Pair-wise competition between staphylococci expressing wtCas9 or hCas9. The change in the relative frequency of cells carrying the hcas9 allele (y-axis) is plotted against the number of culture transfers (one transfer per day, x-axis).

Figure 1:
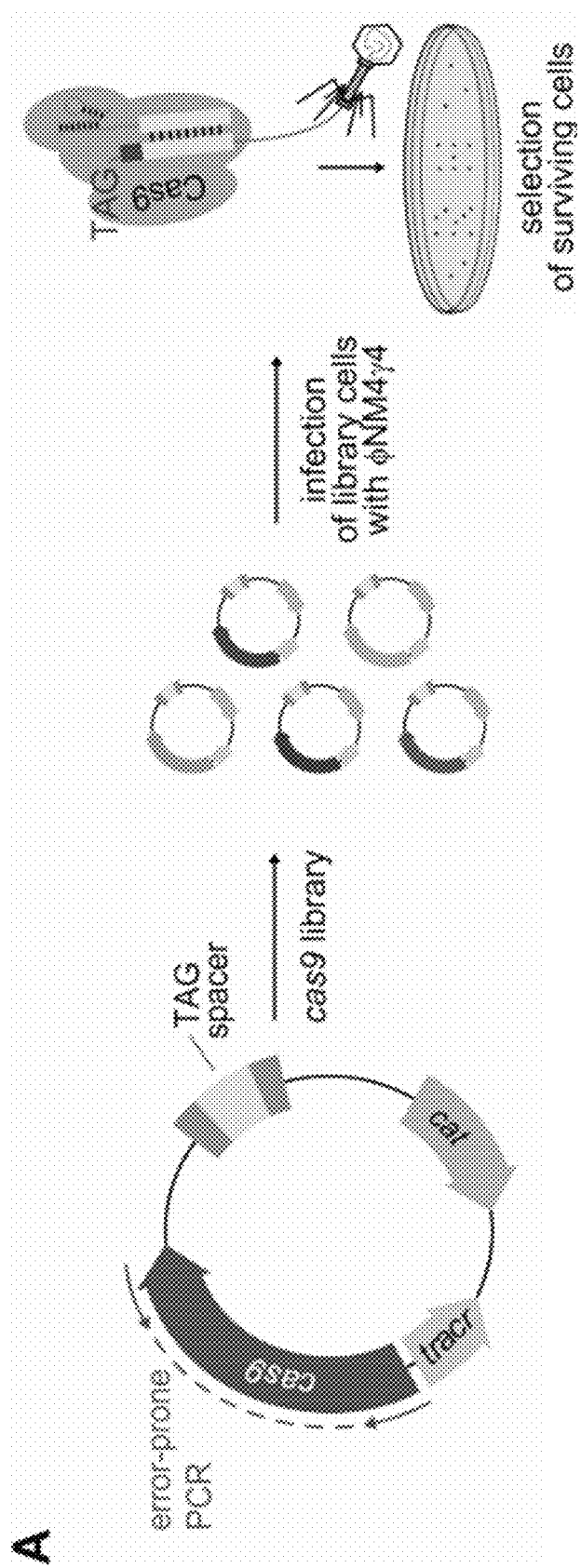
FIG. 1. Directed evolution of cas9 generates mutants with increased specificity for NAG targets. See also FIG. 5. (A)
Figure 1:
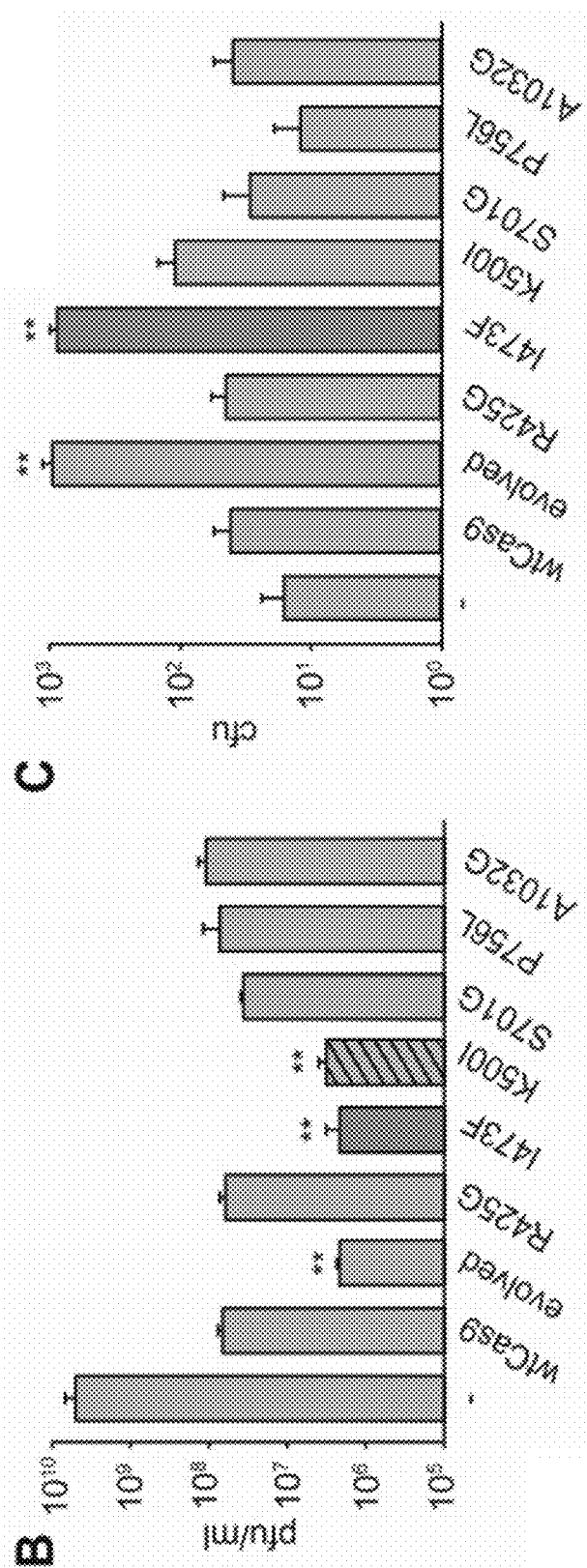
Figure 1:
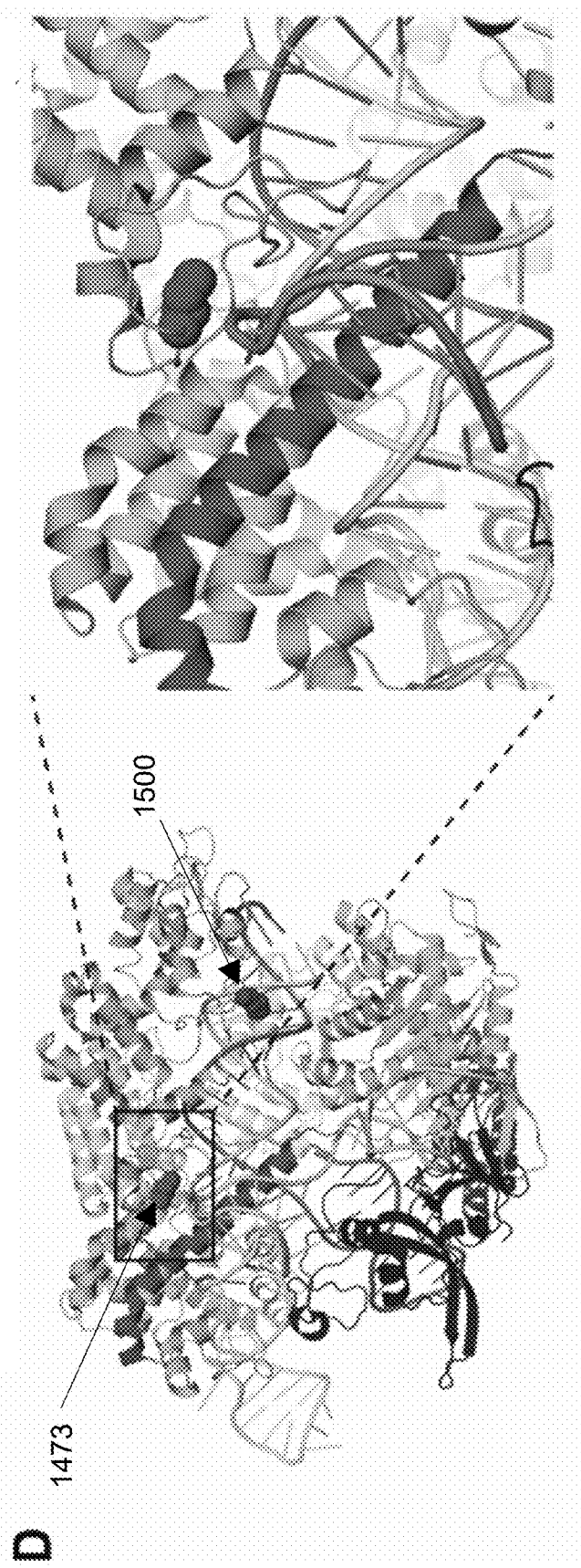
Figure 5:
Figure 5:
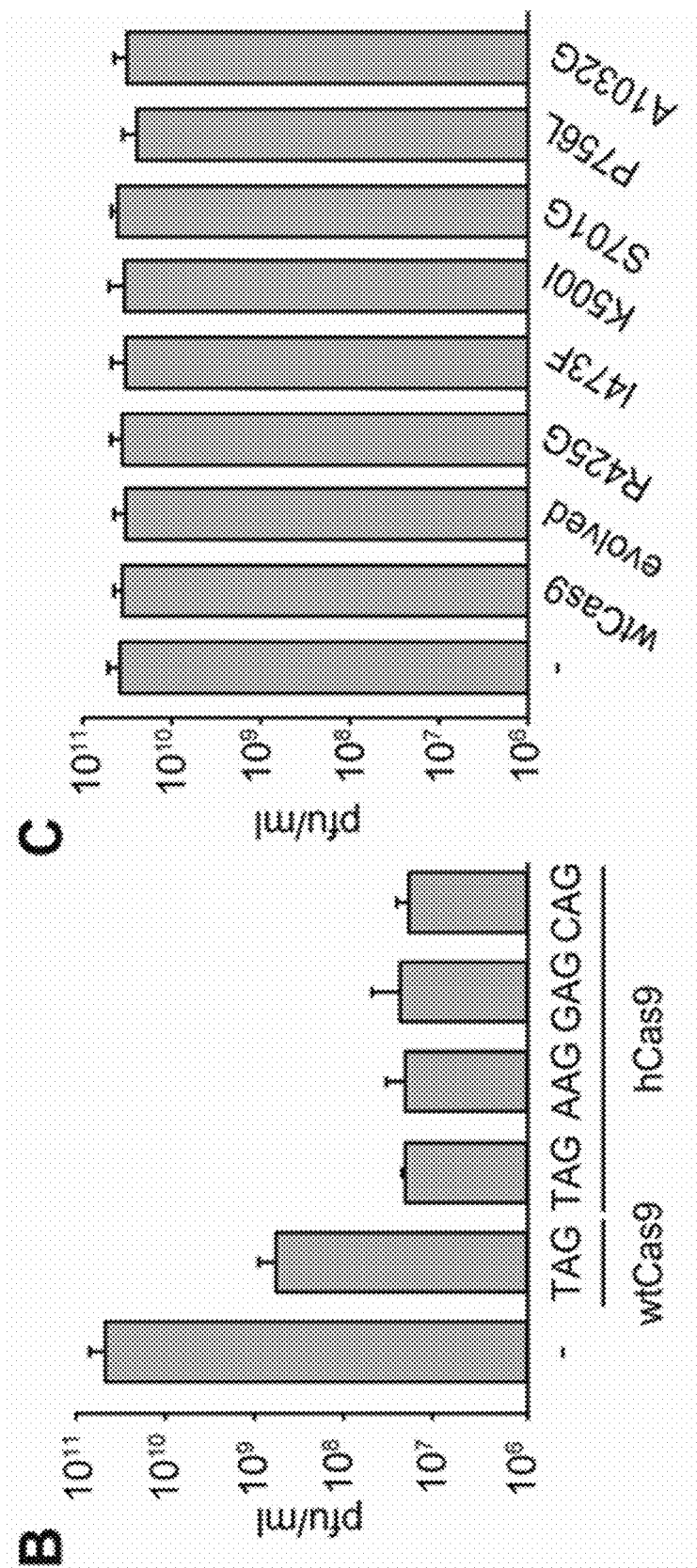
Figure 5:
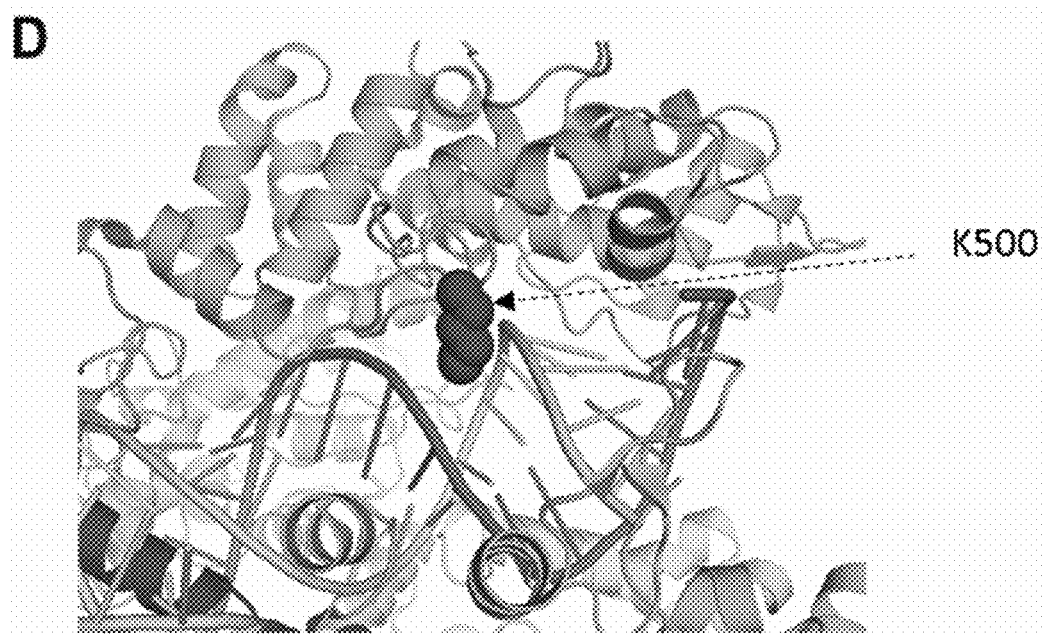

FIG. 5. Protection of host cells by hCas9 programmed against different NAG-flanked targets. Related to FIG. 1. (A) The ability of hCas9 to target protospacers with different PAM was tested by measuring phage propagation in cells harboring CRISPR-Cas systems containing either wtCas9 or hCas9 and programmed to target the sequences shown, which are followed by TAG, AAG, GAG or CAG PAMs. The sequences listed in this figure are SEQ ID NO:128, SEQ ID NO:129, and SEQ ID NO:130. (B) Phage propagation was measured as the number of plaque forming units (pfu) per ml of stock, on cells targeting the TAG, AAG, GAG, and CAG-adjacent protospacers and hCas9. Data are represented as mean±SD of three representative biological replicates. (C) Measurement of pfu formation on staphylococci carrying plasmids with different cas9 mutations after infection with ϕ85, a phage lacking the target recognized in ϕNM4γ4. Data are represented as mean±SD of three representative biological replicates. (D) Location of residue K500 on the Cas9:single-guide RNA ribonucleoprotein (PDB 4UN3). Purple, K500; orange, sgRNA; green, target DNA (the GG PAM highlighted in red); grey, alpha-helical (REC) lobe; yellow, HNH domain; light blue, RuvC domain; blue, PAM-interacting CTD.

Figure 6:
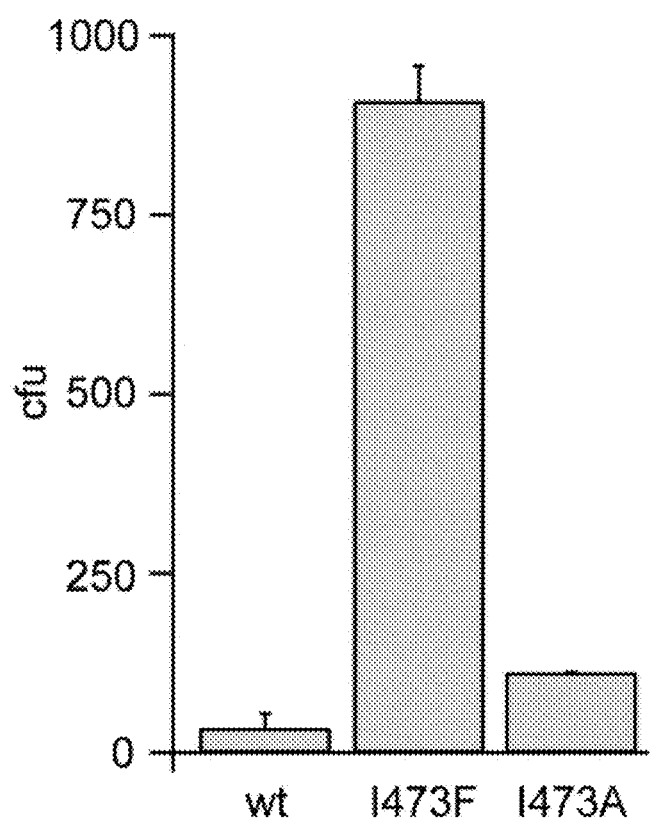

FIG. 6. CRISPR-Cas immune response of cells expressing Cas9$^{I473A}$. Related to FIG. 2. Cultures harboring plasmids with tracrRNA, cas1, cas2 and csn2 genes, and either wild-type, I473F or I473A cas9 alleles, were infected with ΦNM4γ4 phage on top agar media and poured on plates. After 24 hours of incubation at 37° C. the CRISPR-surviving colonies were counted. Data are represented as mean±SD of three representative biological replicates.

Figure 7:
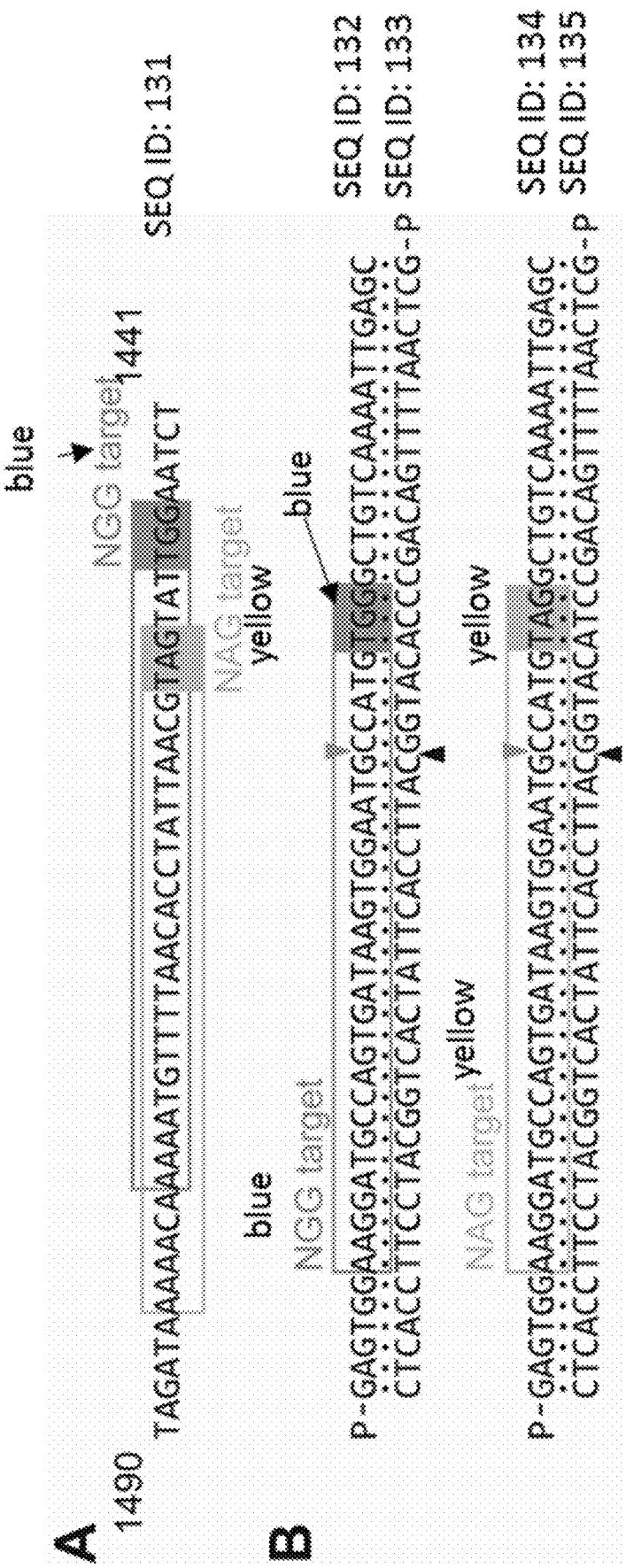

FIG. 7. In vivo and in vitro targets. Related to FIG. 3. (A) Region of the ΦNM4γ4 phage genome (nucleotides 1441 to 1490) containing the TAG- and TGG-flanked protospacers, yellow and blue respectively, used in FIGS. 3A and 3B. This figure contains SEQ ID NO:131. (B) Sequences of the dsDNA target oligonucleotides used in FIG. 3C. The protospacer sequence is the same, but it is flanked by either a TAG (yellow) or TGG (blue) PAM sequence. Radiolabel is at the 5' end (P). Grey and black arrowheads mark the cleavage sites of the RuvC and HNH domains, respectively. This figure contains SEQ ID NO:132, SEQ ID NO:133, SEQ ID NO:134, and SEQ ID NO:135.

Figure 8:
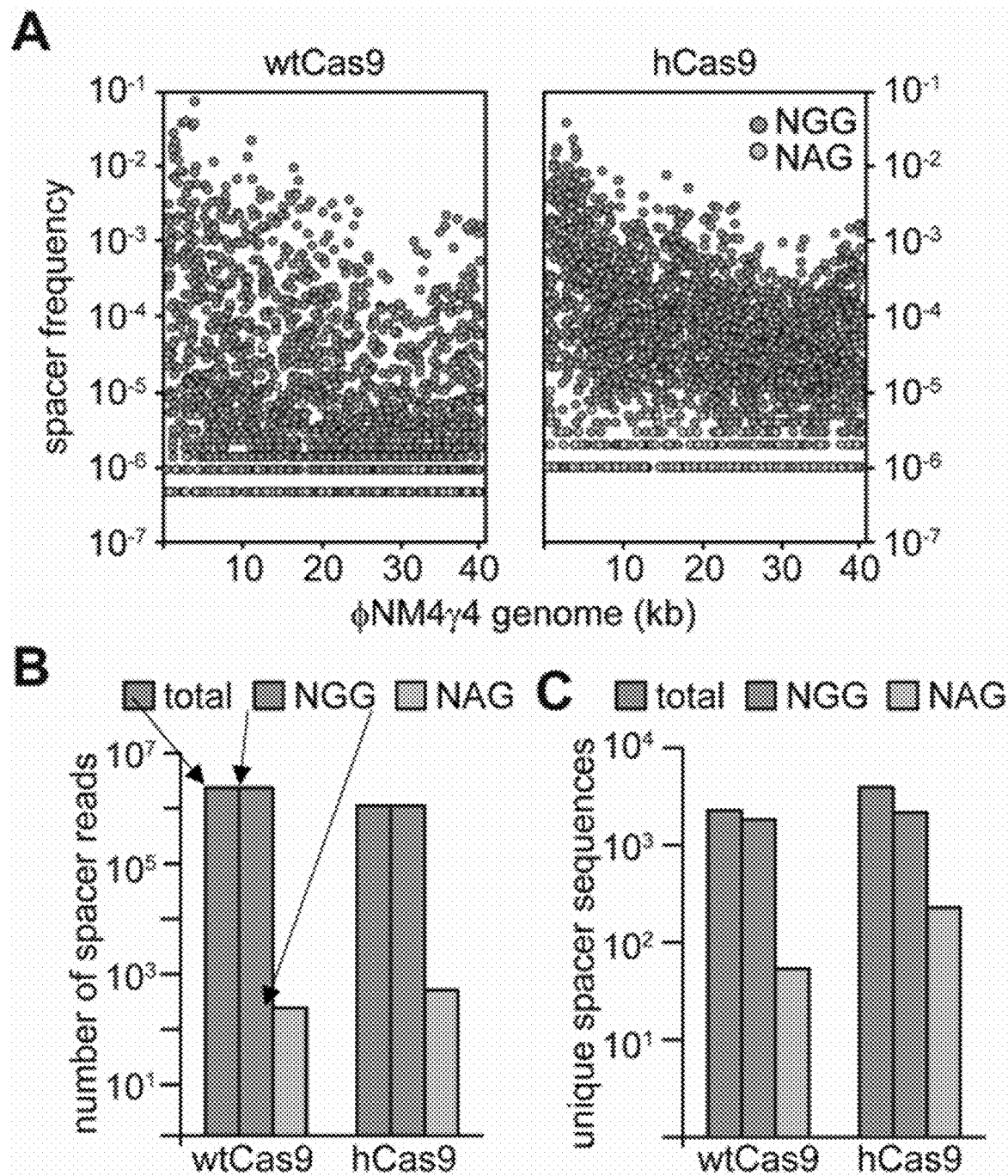
Figure 8:
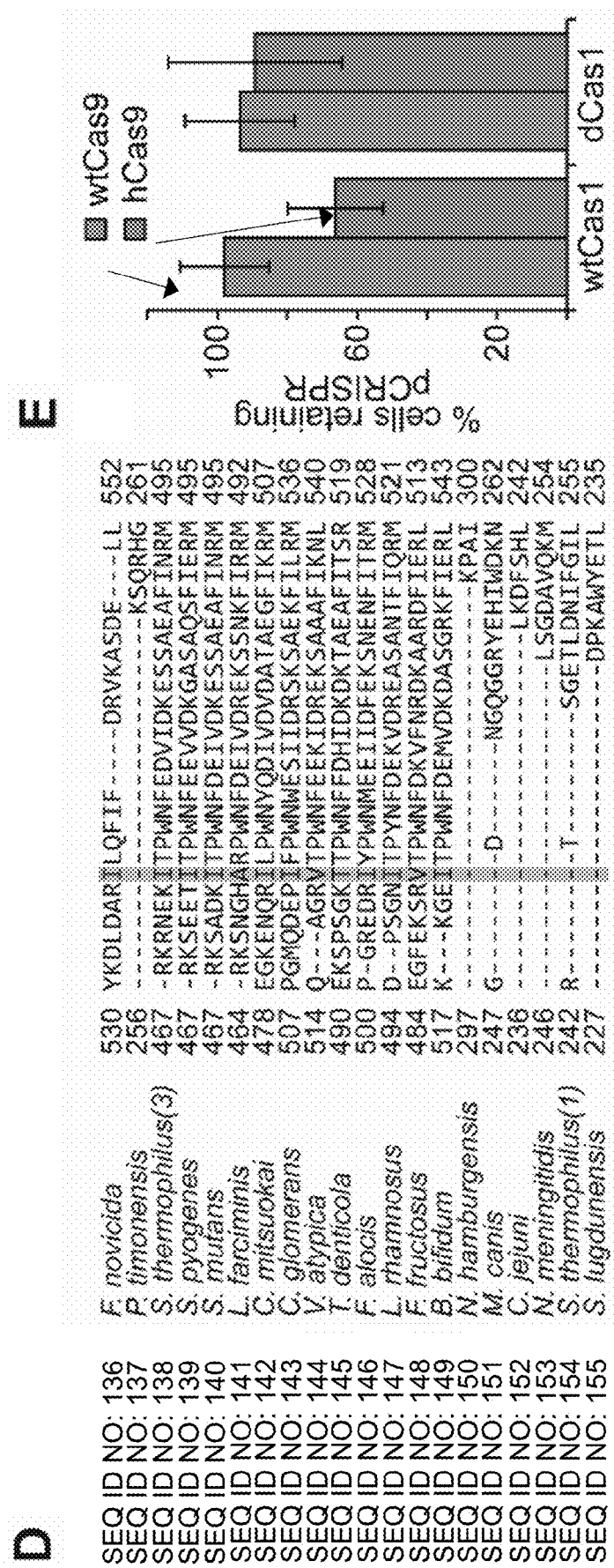

FIG. 8. Analysis of next-generation sequencing results. Related to FIG. 4. (A) Data presented in FIG. 4B and in Supplementary Data File was plotted as the number of reads for each spacer sequence across the phage genome, normalized by the total number of spacer reads obtained. Spacers matching protospacers with NGG PAMs are shown in blue, with NAG PAMs in yellow. (B) Quantification of the data shown in panel A.
(C) Quantification of the data shown in FIG. 4B. (D) Alignment of Cas9 protein sequences belonging to type II CRISPR-Cas systems. Highlighted in orange is the I473 residue. An equivalent residue is not found in some type II-B and II-C systems. This figure contains SEQ ID NO:136, SEQ ID NO:137, SEQ ID NO:138, SEQ ID NO:139, SEQ ID NO:140, SEQ ID NO:141, SEQ ID NO:142, SEQ ID NO:143, SEQ ID NO:144, SEQ ID NO:145, SEQ ID NO:146, SEQ ID NO:147, SEQ ID NO:148, SEQ ID NO:149, SEQ ID NO:150, SEQ ID NO:151, SEQ ID NO:152, SEQ ID NO:153, SEQ ID NO:154, and SEQ ID NO:155. (E) Fraction (%) of staphylococci retaining the plasmid harboring wtcas9 and hcas9 after 10 days of culture; with one transfer (1:100 dilution into fresh media) per day. Cells were plated in solid media with and without chloramphenicol, an antibiotic that selects for cells harboring the pCRISPR plasmid. The fraction of staphylococci carrying this plasmid was obtained dividing the chloramphenicol-resistant cfu by the total cfu count. Data are represented as mean±SD of three representative biological replicates.

Figure 9:
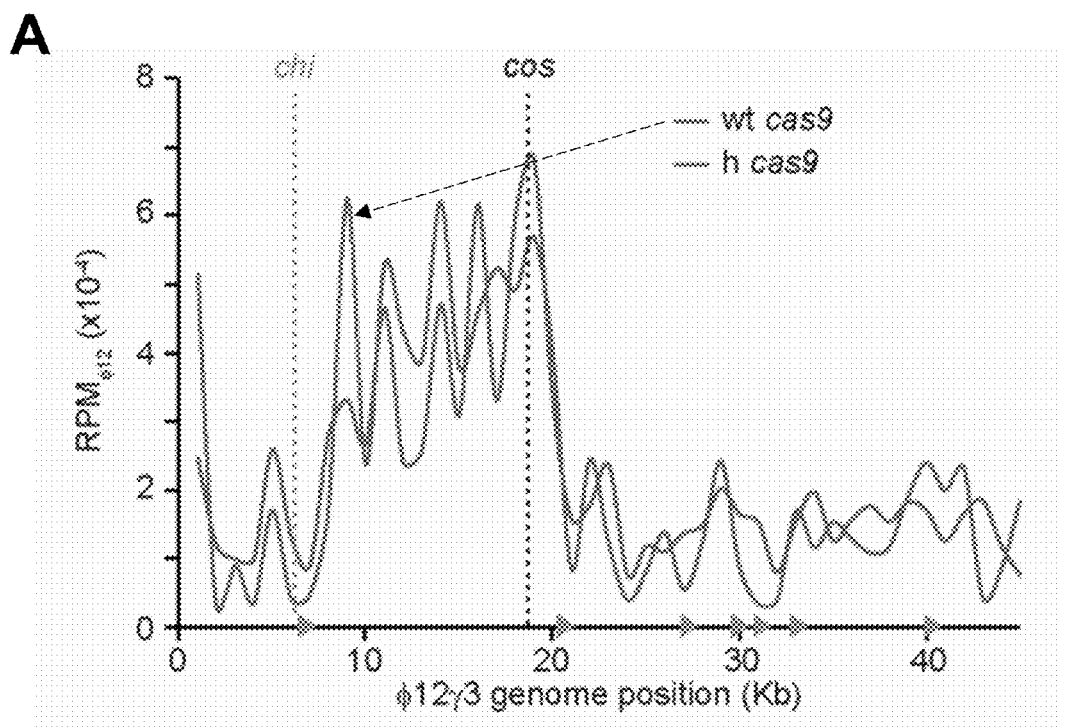
Figure 9:
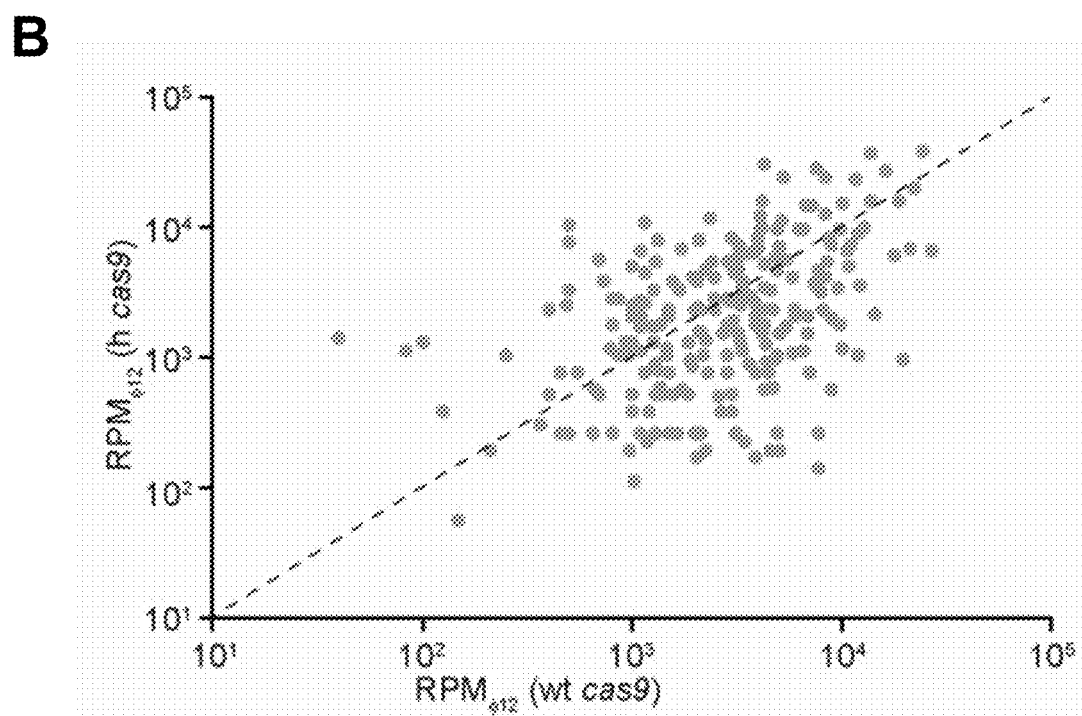

FIG. 9. Patterns spacer acquisition from the virus ϕ12γ3 using hyper or wt cas9. A, Abundance ($RPM_{\phi12}$) of ϕ12γ3 sequences incorporated into the CRISPR array after a 30 minute infection at MOI 100 of cells harboring h cas9 (purple) or wt cas9 (green). B, Individual spacers common to both datasets in panel c were plotted with $RPM_{\phi12}$ values for h cas9 on the y-axis and wt cas9 on the x-axis. cos, cohesive end; chi, first chi site upstream of the cos site. The diagonal dotted line indicates the identity line.

DETAILED DESCRIPTION

Unless defined otherwise herein, all technical and scientific terms used in this disclosure have the same meaning as commonly understood by one of ordinary skill in the art to which this disclosure pertains.

Every numerical range given throughout this specification includes its upper and lower values, as well as every narrower numerical range that falls within it, as if such narrower numerical ranges were all expressly written herein.

The disclosure includes all polynucleotide sequences described herein, including RNA and DNA equivalents of each of the sequences, their complementary sequences, their reverse sequences, and the reverse complements of the sequences, and proteins encoded by the sequences, including polynucleotides encoding proteins described herein.

The present disclosure provides compositions and methods that relate in general to novel Cas9 enzymes, referred to herein as "hyper Cas9" and "hCas9". The disclosure includes isolated Cas9 enzymes, cells comprising/expressing the novel Cas9 enzymes, including but not necessarily limited to populations of bacterial cells and their progeny, polynucleotide sequences and expression vectors encoding the novel Cas9 enzymes, kits comprising expression vectors encoding the novel Cas9 enzymes, and/or cells expression the novel Cas9 enzymes. Methods of making cells that express the novel Cas9 enzymes for numerous purposes are provided and are described further below. gRNAs and/or expression vectors/polynucleotides encoding them can optionally be included in compositions, kits and products of this disclosure. In embodiments, expression vectors can encode any suitable activating crRNA (tracrRNA) gene, or another expression vector can be included to express the crRNA.

The novel hCas9 enzymes of this disclosure are functionally and structurally distinct from their naturally occurring counterparts. Structurally hCas9 enzymes differ in amino acid sequence from wild type Cas9. Functionally, the hCas9 enzymes have at least one of the following properties relative to their wild type counterparts: i) increased rate of spacer acquisition, ii) increased cleavage efficiency of targets with NAG PAMs.

In embodiments, an hCas9 of this disclosure comprises a modified *Streptococcus pyogenes* hCas9. In embodiments, the modification comprises a substitution of at least one of the following amino acids: I473 and K500. It is believed any substitution of these amino acids can be made, provided the modified Cas9 exhibits at least one of i) increased rate of spacer acquisition, and ii) increased cleavage efficiency of targets with NAG PAMs. In embodiments, conservative amino substitutions are made. In certain embodiments the amino acid changes comprise at least one of I473F, I473A and K500I. These amino acids have positions according to the known reference sequence of *S. pyogenes*, which is available under GenBank accession no. NC 002737, with the cas9 gene at position 854757-858863. The *S. pyogenes* Cas9 amino acid sequence is available under number is NP_269215. These sequences are incorporated herein by reference as they were provided in the database on the priority date of this application or patent. In embodiments, the disclosure encompasses making the same or similar amino acid changes in Cas9 enzymes that are from bacteria other than *S. pyogenes*, including but not necessarily limited to *S. aureus* Cas9. In an embodiment, the mutations are present in a Cas9 amino acid sequence that comprises between 80-99% similarity to the following sequence, so long as the modified Cas9 includes at least one of the properties described above, e.g., i) increased rate of spacer acquisition, and ii) increased cleavage efficiency of targets with NAG PAMs:

(SEQ ID NO: 1)

```
  1  mdkkysigld igtnsvgwav itdeykvpsk kfkvlgntdr hsikknliga llfdsgetae 61  atrlkrtarr rytrrknric ylqeifsnem akvddsffhr leesflveed kkherhpifg 121  nivdevayhe kyptiyhlrk klvdstdkad lrliylalah mikfrghfli egdlnpdnsd 181  vdklfiqlvq tynqlfeenp inasgvdaka ilsarlsksr rlenliaqlp gekknglfgn 241  lialslgltp nfksnfdlae daklqlskdt ydddldnlla qigdqyadlf laaknlsdai 301  llsdilrvnt eitkaplsas mikrydehhq dltllkalvr qqlpekykei ffdqskngya 361  gyidggasqe efykfikpil ekmdgteell vklnredllr kqrtfdngsi phqihlgelh 421  ailrrqedfy pflkdnreki ekiltfripy yvgplargns rfawmtrkse etitpwnfee
```

```
-continued
 481  vvdkgasaqs  fiermtnfdk  nlpnekvlpk  hsllyeyftv  yneltkvkyv  tegmrkpafl 541  sgeqkkaivd  llfktnrkvt  vkqlkedyfk  kiecfdsvei  sgvedrfnas  lgtyhdllki 601  ikdkdfldne  enedilediv  ltltlfedre  mieerlktya  hlfddkvmkq  lkrrrytgwg 661  rlsrklingi  rdkqsgktil  dflksdgfan  rnfmqlihdd  sltfkediqk  aqvsgqgdsl 721  hehianlags  paikkgilqt  vkvvdelvkv  mgrhkpeniv  iemarenqtt  qkgqknsrer 781  mkrieegike  lgsqilkehp  ventqlqnek  lylyylqngr  dmyvdqeldi  nrlsdydvdh 841  ivpqsflkdd  sidnkvltrs  dknrgksdnv  pseevvkkmk  nywrqllnak  litqrkfdnl 901  tkaergglse  ldkagfikrq  lvetrqitkh  vaqildsrmn  tkydendkli  revkvitlks 961  klvsdfrkdf  qfykvreinn  yhhandayln  avvgtalikk  ypklesefvy  gdykvydvrk 1021  miakseqeig  katakyffys  nimnffktei  tlangeirkr  plietngetg  eivwdkgrdf 1081  atvrkvlsmp  qvnivkktev  qtggfskesi  lpkrnsdkli  arkkdwdpkk  yggfdsptva 1141  ysvlvvakve  kgkskklksv  kellgitime  rssfeknpid  fleakgykev  kkdliiklpk 1201  yslfelengr  krmlasagel  qkgnelalps  kyvnflylas  hyeklkgspe  dneqkqlfve 1261  qhkhyldeii  eqisefskry  iladanldkv  lsaynkhrdk  pireqaenii  hlftltnlga 1321  paafkyfdtt  idrkrytstk  evldatlihq  sitglyetri  dlsqlggd
```

The disclosure includes methods for using the novel Cas9 enzymes for a wide variety of purposes, including but not necessarily limited to increasing frequency of CRISPR spacer acquisition, labeling cells that have been modified by spacer acquisition, detecting cells that have been labeled accordingly, the labeled cells themselves, and increasing the efficiency of CRISPR target editing. In embodiments the disclosure comprises improved approaches to Cas9/CRISPR immunization of populations of bacteria against infection by one or more distinct types of bacteriophages. Thus, it is expected that any Cas9-implemented method or approach, whether now known or hereafter developed, will benefit from including a novel Cas9 of this disclosure. The disclosure also includes a wide variety of products, including but not necessarily limited to cell products and food products that have been directly or indirectly exposed to a novel Cas9 of this disclosure, or to bacteria that express such a Cas9. In this regard, the disclosures of U.S. patent publication no. 20150093473, U.S. patent publication no. 20130158245, and U.S. Pat. Nos. 7,919,277, 8,361,725, and 9,399,801 are incorporated herein by reference. In embodiments, a novel Cas9 enzyme of this disclosure is used as a substitute for, or in addition to, any CRISPR-based system and/or CRISPR based methods disclosed in any of these patent publications and patents.

In certain approaches the disclosure comprises modified bacteria that express a novel Cas9 enzyme of this disclosure. In embodiments, the disclosure includes modified gram negative bacteria that expresses a novel Cas9 enzyme. In embodiments, the disclosure includes modified bacteria that are facultative anaerobes. In embodiments the modified bacteria are gram positive bacteria that expresses a novel Cas9 enzyme of this disclosure. In embodiments the gram positive bacteria are members the *Lactobacillus* genus, and in particular *Lactobacillus* species that are active in the production of food products intended for human and/or non-human animal consumption. In non-limiting embodiments the modified bacteria are *Lactobacillus* species that are active in the production of dairy products, such as yogurt, milk, milk-based creams, ice cream products, and cheese, or fermented drinks, such as wine, cider and beer, or fermented foods, or combinations of the foregoing. In certain embodiments the modified bacteria are *L. plantarum, L. casei, L. acidophilus, L. salivarius*, or *L. reuteri* as well as probiotic strains of *Bifidobacterium* (i.e. *B. longum*).

In embodiments the disclosure includes combinations of modified bacteria described herein, and further comprises combinations of the modified bacteria with other microorganisms, such as yeasts. Those skilled in the art will recognize that such combinations are useful for production of certain foods.

In another aspect the disclosure comprises a food product comprising a modified bacteria that expresses a novel Cas9 enzyme of this disclosure. Such products include all of the aforementioned types of food and modified bacteria. In embodiments the food product is a dairy product, including but not necessarily limited to yogurt, milk, milk-based creams, and cheese. Use of microorganisms in making foods that intentionally contain live cultures, such as yogurts, are well known in the art and can be adapted for use with the presently provided modified microorganisms. In embodiments the food product is intended to, is undergoing, or has undergone a fermentation process. In one aspect the food product is a non-human animal feed.

In certain aspects the disclosure provides a product, such as a food product, which comprises packaging, such as a paper or cardboard carton, a plastic container, bottle, bag, etc., that are typically used for containing foods. The packaging can provide printed material, which includes information that identifies the modified bacteria present in the food product. Bacterial culture containers with such labels are also included in products and kits of this disclosure.

In another aspect the disclosure includes a supplement product, such as a nutraceutical product, a dietary supplement, a food ingredient, etc., including but not limited to a probiotic formulation or functional food that contains one or more live modified bacteria as described herein. The supplement product can be provided in the form of, for example, a liquid, capsules, tablets, softgels, powders, freeze-dried compositions, and the like. These products can have similar labeling as discussed above.

In an embodiment the disclosure includes making modified bacteria that express a novel Cas9 enzyme for use in a variety of purposes, including but not limited to inhibiting bacteriophage infections. The method comprises introducing into bacteria a heterologous DNA sequence encoding a novel Cas9 enzyme, and culturing the bacteria for use in, on or during production of any product described herein or as would otherwise be apparent to one skilled in the art given the benefit of this disclosure, including but not necessarily limited to food and beverage products, and as a probiotics, or nutraceuticals. In embodiments, the bacteria are bacteria used in any industrial application, including but not necessarily limited to biofuel production, petroleum spill cleanup, as well as in the production of cosmetics, pharmaceuticals and construction materials.

In embodiments, the disclosure comprises modified bacterial cultures themselves. In embodiments, the cultures are propagated as, for example, a yogurt culture. In certain embodiments, the disclosure provides a bacteria starter culture that comprises a novel Cas9 enzyme of this disclosure, and may include progeny of such a starter culture, even if the progeny do not maintain the Cas9 enzyme or an expression vector encoding it.

Bacteria modified according to this disclosure can comprise any suitable expression vector that encodes a novel Cas9 enzyme described herein. Such expression vectors can comprise typical components, such as cloning sites, selectable markers, origins or replication, promoters, expression/secretion signals, purification signals, etc. Commercially available vectors can be adapted to express the novel Cas9 enzymes. In embodiments, the disclosure includes use of a tracrRNA. The tracrRNA can comprise a segment that is complementary to a pre-crRNA, such that a portion of the tracrRNA and pre-crRNA can form an RNA duplex. The RNA duplex is cleaved by RNase III, resulting in the formation of a crRNA/tracrRNA hybrid complex. This hybrid functions as a guide for Cas, which cleaves a target sequence. In general, a tracrRNA used in embodiments of the present disclosure will comprise or consist of from 40 to 200 nucleotides, inclusive, and including all integers and ranges there between. There are a wide variety of publicly available resources that can be used to design suitable tracrRNA sequences and such tracrRNA sequences can be adapted for use with embodiments of the present disclosure. In general a mature crRNA, meaning a crRNA that is complexed with a Cas9 enzyme during cleavage of a DNA target sequence, will comprise or consist of from 20-60 nucleotides. In embodiments, a crRNA comprises or consists of 20, 21, 22, 23, 24, 25, 26, 27, 28, 29, or 30 nt of the spacer (targeting) sequence followed by 19-22 nt of repeat sequence.

In one approach the disclosure comprises introducing into bacteria an expression vector encoding a novel Cas9 enzyme of this disclosure, wherein the bacteria exhibit increased spacer acquisition relative to a suitable control, and/or exhibit inhibition of phage propagation in an amount greater than a suitable control. The control can be, for example, the rate of spacer acquisition and/or inhibition of phage propagation achieved by bacteria expressing a wild type Cas9 enzyme, or a modified Cas9 enzyme that does not comprise at least one of I473F or K500I mutations described herein. In this regard, we demonstrate in this disclosure that Cas9 mutants comprising other mutations, such as R425G, S701G, P756L and A1032G, show wild-type levels of phage propagation and therefore do not contribute to the gain-of-function-phenotype of the cas9 alleles that are subjects of this disclosure. Notably, modified bacteria comprising Cas9 with the I473F or K500I mutations decrease phage propagation by about four orders of magnitude. We also demonstrate enhanced phage immunity against NGG-flanked targets as well as other NAG PAMs, such as AAG, CAG, and GAG. Thus, it will be recognized that the I473F and K500I mutations enhance the ability of Cas9 to recognize targets with NAG flanking PAMs and are broadly applicable to spacer acquisition and inhibition of a wide spectrum of bacteriophage types.

In one embodiment, the disclosure comprises separating a plurality of bacteriophage from a bacteria population, wherein the bacteria population may comprise bacteria that either do not express a Cas9 enzyme, or express a Cas9 enzyme that is distinct from a novel Cas9 enzyme of this disclosure. The separated phage can be used directly, or isolated and purified to any desired degree of purity, processed, propagated and/or otherwise processed, and then used to infect a population of bacteria that express a novel Cas9 enzyme of this disclosure. Due to the increased spacer acquisition capabilities of these modified bacteria, it is expected that they will become immunized against a plurality of the phage more efficiently than bacteria that express an unmodified Cas9. In certain embodiments, the modified bacteria may become immunized against a broader diversity of phage as compared to bacteria that express an unmodified Cas9. In an embodiment, the disclosure comprises culturing the immunized bacteria to provide an immunized bacteria population. In certain implementations, the immunized bacteria comprise a starter culture for use production of any product described herein. In embodiments, the starter culture is used for the production of dairy products that are otherwise susceptible to phage infection. In embodiments, the disclosure provides bacteria cultures that comprise bacteria that are resistant to phage infection. In embodiments, the cultures can comprise from 10%-100% phage-resistant bacteria, wherein such resistance can be against a single phage type (i.e., homogenous phage genomes), or against distinct phage types (i.e., heterogeneous phage genomes).

In analyzing the role of Cas9 in spacer acquisition, we analyzed its PAM specificity. We tested in vivo cleavage of targets having the same protospacer sequence but different PAMs displaying all possible trinucleotide combinations (Jiang et al., 2013). We found that, in addition to the complete cleavage of targets with NGG PAMs, wild-type Cas9 displays approximately 50% of in vivo cleavage of targets with NAG PAMs. In an effort to understand how Cas9 affects the acquisition of spacers flanked by NGG motifs, we evolved this weak but detectable affinity of the nuclease for NAG PAMs. After structural analysis determined the PAM interacting domain of Cas9 (Anders et al., 2014; Jinek et al., 2014), different groups have specifically mutated this domain to obtain a versatile set of nucleases for genome editing purposes and have obtained an NAG-recognizing Cas9 (Kleinstiver et al., 2015b). In the present disclosure we took a different approach and searched for mutations in any region of the nuclease that would increase its specificity for NAG-flanked targets. We found one such mutation, I473F, which provided partial immunity when Cas9 was programmed to recognize an NAG viral protospacer; i.e. loaded with the complementary crRNA guide. This mutation also expanded the levels of the CRISPR-Cas adaptive immune response, increasing the number of CRISPR-mediated, bacteriophage-resistant colonies by more than two orders of magnitude. We performed experiments to understand the molecular basis of the enhanced CRISPR-Cas immunity and determined that the I473F mutation mediates a significant increase in spacer acquisition.

Our results highlight the role of Cas9 during CRISPR immunization and provide a useful tool to study this otherwise rare process, as well as for use in the compositions and methods described above.

The following examples are presented to illustrate the present disclosure. They are not intended to be limiting in any manner. In some aspects, these Examples include routine techniques and methods used in the field of genetic engineering and molecular biology that are not otherwise described. The following resources include descriptions of general methodology useful in accordance with the invention: Sambrook et al., Molecular Cloning: A Laboratory Manual (4th Ed., 2012); Kreigler, Gene Transfer and Expression: A Laboratory Manual (1993) and Ausubel et al., Eds. Current Protocols in Molecular Biology (1995). These general references provide definitions and methods known to those in the art. However, it is not intended that the present disclosures be limited to any particular methods, protocols, and reagents described, as these may vary in ways that will be understood by the skilled artisan. Hypothesis described herein are not intended to constrain the disclosure to any particular theory.

Example 1

Directed Evolution of Cas9 Yields a Mutant with Altered PAM Specificity and Enhanced CRISPR-Cas Immunity.

S. pyogenes Cas9 has an innate ability to cleave NAG-adjacent targets, but with much lower efficiency than it cleaves canonical (NGG) targets (Jiang et al., 2013). To improve its specificity for NAG PAMs, we constructed a library of plasmids carrying cas9 variants generated by error-prone PCR (FIG. 1A). The library plasmids also harbor the trans-activating crRNA (tracrRNA) gene (Deltcheva et al., 2011) and a single-spacer CRISPR array targeting a TAG-adjacent protospacer on the genome of the lytic staphylococcal bacteriophage φNM4γ4 (Goldberg et al., 2014). The library was transformed into *Staphylococcus aureus* RN4220 cells that were subjected to two rounds of phage infection on soft-agar plates to select for phage-resistant bacterial colonies. Several colonies were obtained and we proceeded with a more extensive analysis of one of the "evolved" mutants that gained phage resistance. Sequencing of the plasmid revealed the presence of six single-nucleotide substitutions in the cas9 gene (see Extended Experimental Procedures) producing the following missense mutations: R425G, I473F, K500I, S701G, P756L and A1032G. To evaluate the importance of each of these mutations in the gain-of-function phenotype we introduced them individually into the cas9 gene and tested the ability of the resulting plasmid to prevent φNM4γ4 propagation by measuring the number of plaque forming units (pfu) that result after infection of the host cells (FIG. 1B). Cas9 harboring the R425G, S701G, P756L and A1032G mutations allow wild-type levels of phage propagation and therefore do not contribute to the gain-of-function-phenotype of the evolved cas9 allele we isolated. In contrast, cells containing Cas9 with the I473F or K500I mutations decrease phage propagation by about four orders of magnitude. This is close to the levels of immunity provided by wild-type Cas9 when programmed against NGG-flanked targets (a reduction of 5 orders of magnitude, see FIG. 3B). Similar results were obtained when other NAG PAMs were tested (AAG, CAG, GAG, FIGS. 5A-B). Therefore the I473F and K500I mutations enhance the ability of Cas9 to recognize targets with NAG PAMs. The pfu count was similar in all mutant and control strains when infected with φ85, a lytic phage that lacks the target sequence (FIG. 5C), corroborating that the decrease in phage propagation observed for the I473F and K500I mutations is a direct consequence of Cas9 targeting and not due to cell toxicity induced by the various mutants.

Given the requirement of Cas9 for the immunization phase of the CRISPR-Cas immune response, i.e. the acquisition of virus-derived spacer sequences (Heler et al., 2015; Wei et al., 2015), we wondered whether the evolved Cas9 as well as the individual mutants affected this process. To test this, we introduced the different alleles of cas9 into a plasmid harboring the tracrRNA gene, the *S. pyogenes* SF370 CRISPR array (containing six spacers, none of them matching the genome of φNM4γ4) and the type II-A genes exclusively involved in the acquisition of new spacers, cas1, cas2 and csn2 (Heler et al., 2015; Wei et al., 2015). *S. aureus* cells containing the different plasmids were infected with φNM4γ4 and the number of survivors were enumerated as colony forming units (cfu) (FIG. 1C). Only a small fraction of cells containing wild-type Cas9 are able to acquire new spacers, about 2-fold over a CRISPR-less control. In contrast, the evolved cas9 allele containing all six mutations increased the number of CRISPR-surviving cells by about 60-fold. Analysis of single mutants revealed that this highly significant increase was provided almost exclusively by the I473F mutation (FIG. 1C). Due to the sharp enhancement of the CRISPR-Cas immune response conferred by the I473F mutation we decided to name the Cas9$^{I437F}$ mutant "hyper-Cas9", or hCas9. I473 is located close to the surface of Cas9, outside of the PAM-interacting domain, and it is part of a projection from the Helical III domain that interacts with the nexus of the guide RNA (Jiang et al., 2016) (FIG. 1D). This position does not suggest an evident effect of the I473F mutation on Cas9 activity and therefore we decided to investigate the basis for its phenotype by performing a detailed comparison with the CRISPR-Cas immune response mediated by wild-type Cas9.

Example 2 hCas9 Enhances the CRISPR-Cas Adaptive Immune Response by Two Orders of Magnitude.

To perform a more accurate comparison between wild-type (wtCas9) and hCas9, we counted the number of CRISPR-mediated, phage resistant cells that arise after phage infection. FIG. 2A shows representative plates of infected cells containing plasmids with the wtCas9 or hCas9 *S. pyogenes* CRISPR-Cas locus, showing a striking difference in the number of surviving colonies. Most of these colonies arise from single cells that were able to acquire a new spacer matching the φNM4γ4 genome. However, a fraction of the surviving cells repel phage attack by non-CRISPR related mechanisms, such as envelope resistance (Heler et al., 2015). To make a more accurate quantification of the CRISPR-Cas response, we analyzed individual colonies by PCR of the CRISPR array (Heler et al., 2015; Yosef et al., 2012) to detect those in which new spacers were acquired, i.e. "adapted" cells (FIG. 2B). Not only did many more resistant colonies originated from cells harboring hCas9 (an average of 31 cfu for wtCas9 vs 4,312 cfu for hCas9, FIG. 2C), but also most of them showed CRISPR-mediated phage resistance (23% for wtCas9 vs 90% for hCas9, FIG. 2C). We wondered whether this was a consequence of the specific substitution of I473 by phenylalanine. To test this we introduced an I473A mutation into Cas9 (FIG. 7). We found that cells harboring the I473A mutant produced a number of CRISPR-mediated immune cfu comparable to cells carrying wtCas9, but 10 times lower than the cfu obtained from infection of cells expressing hCas9. Therefore we conclude that the I473F mutation increases the CRISPR-adaptive immune response through a specific effect of the phenylalanine residue in position 473 and by more than two orders of magnitude: on average, approximately 7 cfu (31×0.23) per experiment for infected wtCas9-containing cells, and approximately 3,863 cfu (4,312×0.90) for infected hCas9-expressing bacteria. We sequenced PCR products to determine the PAM of the spacers acquired by 40 colonies expressing wtCas9 (Table 1) or hCas9 (Table 2). Interestingly, all 40 spacers acquired by cells expressing hCas9 matched targets with an NGG PAM, suggesting that this nuclease can still target sequences followed by the canonical PAM in addition to targets with NAG PAMs.

Similar results were observed when cells in culture carrying naïve wtCas9 or hCas9 CRISPR-Cas systems were infected with phage. Upon addition of ϕNM4γ4, the cultures lyse, as the vast majority of cells do not undergo spacer acquisition (FIG. 2D). Nonetheless, hCas9 cultures were able to regrow much earlier (~14 hours post-infection) than wtCas9 cultures (~17 hours post-infection). PCR analysis using DNA extracted from the whole culture at 24 hours post-infection corroborated the earlier observation that hCas9 cells mount a more robust CRISPR immune response (FIG. 2E). Whereas the PCR products derived from wtCas9 staphylococci showed the presence of both adapted and non-adapted CRISPR arrays in the surviving population, the PCR results from cultures carrying hCas9 showed very little non-adapted CRISPR arrays, with the great majority of the cells acquiring one or two new spacers. Altogether these data show that the I473F mutation in Cas9 allows for a more robust CRISPR-Cas immune response due to a specific effect of the phenylalanine residue.

Example 3 hCas9 Displays a Modest Increase in the Cleavage Efficiency of Targets with NAG PAMs.

Next, we analyzed whether the enhanced immunity phenotype of hCas9 documented in FIG. 2 was due to an increase in the frequency of spacer acquisition, a more robust cleavage by hCas9 of its targets, or both. First we considered the possibility that hCas9 could provide better cleavage of the infecting viral DNA. In this scenario both wtCas9 and hCas9 populations can acquire a similar number of new spacers but a more robust cleavage of the target DNA by hCas9 would lead to a faster recovery of the bacteria that acquired the spacers. To test this hypothesis, we infected cells carrying plasmids with either wtCas9 or hCas9 programmed to target the ϕNM4γ4 virus and the tracrRNA gene, but without the spacer acquisition machinery (cas1, cas2 and csn2). This genetic background supports CRISPR-Cas anti-viral defense but does not allow the acquisition of new spacer sequences (Heler et al., 2015). Because our data suggested that hCas9 can still target protospacers followed by NGG PAMs, we tested the immunity of cells programmed to attack targets with either an NAG or an NGG PAM located in the same region of the ϕNM4γ4 genome (FIG. 8A). Bacteria containing different plasmids were infected with phage during exponential growth and the optical density of the culture was followed over time to measure the immunity provided by Cas9 cleavage of the viral genome (FIG. 3A). As expected, cells harboring a vector control were rapidly lysed by the addition of phage. On the other hand, cells expressing wtCas9 or hCas9 programmed against an NGG target cleared the infection efficiently and continued the exponential growth, indicating that the I473F mutation does not affect the recognition and targeting of NGG-flanked sequences. In contrast, both cultures display poor survival when NAG-flanked protospacers were targeted by either Cas9 version, with cells expressing wtCas9 suffering a more substantial lysis than cells expressing hCas9. Similar results were obtained when we tested the same cultures for their ability to limit phage propagation (pfu/ml) (FIG. 3B).

Both in vivo experiments measuring bacterial survival (FIG. 3A) and phage propagation (FIG. 3B) suggest that hCas9 has not improved efficiency of cleavage of NGG-flanked targets, and displays only a small increase in the cleavage of NAG-flanked sequences. To unequivocally demonstrate this, we performed in vitro cleavage assays with purified wtCas9 and hCas9 (FIG. 3C). In this case, we were able to compare cleavage of radiolabeled oligonucleotides containing the same protospacer sequence followed by either a TGG or TAG PAM (FIG. 7B). Consistent with in vivo data, experiments showed similar cutting rates of the NGG target for wtCas9 and hCas9. Quantification of the cleavage products showed that hCas9 cleaved more of the NAG target than wtCas9 over longer timescales (FIG. 3D). Altogether, the data presented in FIG. 3 indicate that while there is a modest increase in the NAG-targeting properties of hCas9, this cannot explain the rise in the number of CRISPR-resistant colonies mediated by the I473F mutation (FIG. 2C).

Example 4 hCas9 Promotes Higher Rates of Spacer Acquisition.

A second hypothesis that could explain the increase in CRISPR-Cas immunity conferred by hCas9 is an increase in the frequency of spacer acquisition by the cells expressing this mutant. To test this we performed a comparison of the spacer repertoires acquired by cells harboring wtCas9 or hCas9. We made two plasmid libraries, carrying the spacer acquisition genes cas1, cas2 and csn2 and wtcas9 or hcas9, the tracrRNA gene and the S. pyogenes CRISPR array preceded by a "barcode" sequence of 10 nucleotides 50 bp immediately upstream of the CRISPR array (FIG. 4A). Cells harboring each library were infected with phage ϕNM4γ4 and DNA from the surviving cells was used to amplify the CRISPR array via PCR and collect sequence information of all the new acquired spacers using next generation sequencing. The primers used also amplify the barcode sequence (FIG. 4A) and therefore each new spacer sequence can be associated with a unique barcode, allowing us to count how many times a given spacer was independently acquired in each bacterial population. Over three million reads belonging to either library were analyzed. The frequency of reads corresponding to each acquired spacer sequence was plotted according to its position in the ϕNM4γ4 genome (FIG. 8A). Analysis of the PAMs of the acquired spacers showed that over 99.5% of the spacers matched NGG targets in both libraries (FIG. 8B), corroborating our in vivo data showing that hCas9 retained NGG PAM specificity. In addition, we looked at the repertoire of unique different spacers independently of the number of reads per sequence (FIG. 8C). Consistent with our previous finding that the PAM specificity of Cas9 is responsible for the PAM sequence of the new protospacers, the hCas9 library showed a 5-fold increase in the acquisition of spacers matching NAG-flanked targets. Even with this increase these spacers represent less than 0.05% of the total acquisition events, most likely due to the fitness cost associated with the low efficiency of NAG-target cleavage observed for hCas9 when compared with its cleavage of NGG targets. We also observed an increase in the total number of different spacer sequences, from 1980 for wtCas9 cells to 2500 for the hCas9 sample. All together, these findings show that hCas9 provides the host bacterium with highly efficient spacer acquisition, thus enhancing CRISPR-Cas immunity.

To calculate the frequency of acquisition of every spacer we divided the number of different barcodes for a given spacer sequence by the total number of reads. This value was plotted according to its position in the φNM4γ4 genome (FIG. 4B). The data show a drastic increase in the frequency of acquisition in hCas9 cells. For all 1938 newly acquired spacer sequences shared between the two libraries, we calculated the ratio of unique adaptation events (i.e. number of different barcodes) for hCas9 reads compared to wtCas9 (FIG. 4C). We found that more than 97% of the spacers were acquired more frequently in the hCas9 library (ratio >1), with an average ratio of ~18. This experiment indicates that hCas9 enhances the rate of spacer acquisition during the CRISPR adaptation phase. To rule out any effect that the phage selection imposed on adapted cells could have on our experiments we looked at the rates of spacer acquisition in the absence of phage infection. Using our barcoded system, we passaged cells expressing wtCas9 or hCas9 for 10 days, and subjected a PCR product containing the CRISPR locus of each culture to next generation sequencing. The frequency of acquisition was one order of magnitude higher for hCas9-expressing cells (FIG. 4D). Altogether, these findings show that hCas9 provides the host bacterium with more efficient spacer acquisition, and suggest that this is a major contributor to the enhanced CRISPR-Cas immunity granted by hCas9.

Higher levels of immunization during the CRISPR-Cas response to phage infection provides better host defense. However, this could also lead to detrimental effects in the absence of infection, leading to high levels of CRISPR "autoimmunity". Consistent with this scenario, the I473F mutation was not found in type II-A cas9 gene variants (FIG. 8D). To explore the possible detrimental effects of hCas9 we looked at the rates of plasmid loss in the absence of phage infection since in our barcoded experiment without viral infection, as well in other similar experiments (Heler et al., 2015; Levy et al., 2015; Yosef et al., 2012), most of the acquired self-spacers match plasmid sequences. To test this we plated cells after 10 days of growth with and without chloramphenicol to calculate the frequency of plasmid loss as the number of chloramphenicol-resistant cfu relative to the total cfu count (FIG. 8E). Whereas most staphylococci expressing wtCas9 maintained the plasmid, about 30% of the cells producing hCas9 lost it. This decrease was dependent on the presence of an active Cas1-Cas2 spacer integrase, demonstrating that plasmid loss was caused by CRISPR autoimmunity. Higher autoimmunity in hCas9-expressing cells resulted in a fitness cost, as shown by pairwise competition assays in which wtCas9- and hCas9-expressing cells were grown together and the relative proportion of each strain was measured over time (staphylococci harboring the hcas9, but not the wtcas9, plasmid also carried an erythromycin-resistance gene in their chromosome). We detected a decrease in the proportion of erythromycin-resistant cfu over time (FIG. 4E), demonstrating that a "hyper-acquiring" type II CRISPR-Cas system confers a fitness cost to the cells that carry it.

It will be apparent from the foregoing that this disclosure provides non-limiting demonstrations of random mutagenesis on the entire cas9 gene and which lead to the identification of a mutant with an expanded CRISPR-Cas response. This "hyper" Cas9 version (hCas9) harbors the mutation I473F. Compared to wild-type staphylococci, cells harboring hcas9 displays a modest increase in NAG-target recognition but a substantial increase (more than two orders of magnitude) in the frequency of spacer acquisition. The molecular mechanism by which the I473F mutation enables this increase in spacer acquisition is not clear. Without intending to be constrained by any particular theory, it is considered that, given its location on the surface of hCas9, F473 could interact with other Cas proteins and increase the abundance or the stability of the complex, thus enhancing the rate of spacer acquisition. To test this we incubated the four proteins along with a single-guide RNA (Jinek et al., 2012) and subjected them to gel filtration to detect the formation of the complex. However, we did not observe significant amounts of stable complexes neither in the presence of wtCas9 nor hCas9. In wtCas9, the isoleucine residue is in direct contact with bases of the tracrRNA (FIG. 1D) that are equivalent to the *nexus* in the single-guide RNA (Briner et al., 2014). Specifically, nucleotide U59 of the tracrRNA inserts into a hydrophobic pocket lined by I473 and its adjacent residues (Jiang et al., 2016). It is possible that the bulkier phenylalanine residue could interfere with the tracrRNA:Cas9 association, affecting the involvement of Cas9 in the immunization step of the CRISPR-Cas response. This hypothesis is supported by the wild-type phenotype of the I473A mutation (FIG. 6), since the smaller alanine residue most likely will not interfere with the tracrRNA interaction. Another mutation in a residue close to I473, K500I, also seems to affect Cas9 target specificity, but not the rate of spacer acquisition. K500 is located in the minor groove of the PAM-distal crRNA-target DNA duplex (FIG. 5D), near the backbone of nucleotide 12 of the DNA protospacer and nucleotide 3 of the crRNA (Anders et al., 2014). The loss of a basic residue in this region might alter target binding and recognition, analogous to the increase in specificity resulting from mutations of other residues making nonspecific DNA contacts (Kleinstiver et al., 2016).

In spite of the enhanced immune response provided by the I473F substitution, we could not find cas9 genes harboring this mutation in the genome of bacteria sequenced so far. Two studies have shown that Cas9 is required for the acquisition of self-targeting spacers (Heler et al., 2015; Wei et al., 2015), a situation that leads to "auto-immunity" and to the death of the host (Bikard et al., 2014; Jiang et al., 2013). Here we show that the enhanced rate of spacer acquisition of hCas9 results in an increase in the autoimmunity events and therefore leads to a fitness cost for the host cell. We believe that this prevents the evolution of the I473F mutation into Cas9.

The phenotype of the I473F mutation in Cas9 further demonstrates the involvement of this nuclease in the acquisition of new spacers in type II CRISPR-Cas systems and provides a new tool that could facilitate the study of CRISPR immunization, making this process more frequent and easier to detect. In addition, hCas9 provides a useful tool for the development of technologies that use the incorporation of spacers to develop synthetic biology devices that can record different cellular events (Shipman et al., 2016). Currently, the low adaptation frequency limits the number of stimuli that can be captured as new spacers in the CRISPR array. Using an enhanced CRISPR adaptation machinery such as hCas9 could boost the spacer acquisition frequency and thus facilitate the development of this and other related synthetic biology technologies.

Example 5

This Example provides a description of the materials and methods used to obtain the results discussed above for FIGS. 1-4.

Bacterial Strains and Growth Conditions

Cultivation of *S. aureus* RN4220 (Kreiswirth et al., 1983) was carried out in heart infusion broth (BHI) at 37° C. Whenever applicable, media were supplemented with chloramphenicol at 10 µg ml$^{-1}$ to ensure pC194-derived plasmid maintenance or 5 mM $CaCl_2$ for phage adsorption.

Directed Evolution of Cas9

The cas9 gene was mutagenized at a low rate of 0-4.5 mutations/kb by error prone PCR using GeneMorph II Random Mutagenesis Kit. The mutant cas9 amplicons were cloned into a backbone plasmid containing a spacer matching a TAG-adjacent target on ϕNM4γ4. The library was subjected to soft-agar lytic phage infection and surviving colonies were re-streaked on fresh plates. The TAG-cleaving efficiency of surviving colonies was individually assessed by phage propagation assays.

High-Throughput Sequencing

Plasmid DNA was extracted from adapted cultures using the in-liquid spacer acquisition assay described in Experimental Procedures. 200 ng of plasmid DNA was used as template for Phusion PCR to amplify the CRISPR locus with primer pairs H372-H373 and H376-H377 (Table 3) for the wtcas9 and hcas9 libraries, respectively. Following gel extraction and purification of the adapted bands, samples were subject to Illumina MiSeq sequencing. Data analysis was performed in Python: first, all newly acquired spacer sequences were extracted from raw MiSeq FASTA data files. Next, the frequency (number of different barcode sequences), the phage target location and the flanking PAM were determined for each unique spacer sequence.

REFERENCES FOR THE FOREGOING DESCRIPTION

Anders, C., Niewoehner, O., Duerst, A., and Jinek, M. (2014). Structural basis of PAM-dependent target DNA recognition by the Cas9 endonuclease. Nature 513, 569-573.

Barrangou, R., Fremaux, C., Deveau, H., Richards, M., Boyaval, P., Moineau, S., Romero, D. A., and Horvath, P. (2007). CRISPR provides acquired resistance against viruses in prokaryotes. Science 315, 1709-1712.

Bikard, D., Euler, C. W., Jiang, W., Nussenzweig, P. M., Goldberg, G. W., Duportet, X., Fischetti, V. A., and Marraffini, L. A. (2014). Exploiting CRISPR-Cas nucleases to produce sequence-specific antimicrobials. Nat. Biotechnol. 32, 1146-1150.

Briner, A. E., Donohoue, P. D., Gomaa, A. A., Selle, K., Slorach, E. M., Nye, C. H., Haurwitz, R. E., Beisel, C. L., May, A. P., and Barrangou, R. (2014). Guide RNA functional modules direct Cas9 activity and orthogonality. Mol. Cell 56, 333-339.

Brouns, S. J., Jore, M. M., Lundgren, M., Westra, E. R., Slijkhuis, R. J., Snijders, A. P., Dickman, M. J., Makarova, K. S., Koonin, E. V., and van der Oost, J. (2008). Small CRISPR RNAs guide antiviral defense in prokaryotes. Science 321, 960-964.

Carte, J., Wang, R., Li, H., Terns, R. M., and Terns, M. P. (2008). Cas6 is an endoribonuclease that generates guide RNAs for invader defense in prokaryotes. Genes Dev. 22, 3489-3496.

Deltcheva, E., Chylinski, K., Sharma, C. M., Gonzales, K., Chao, Y., Pirzada, Z. A., Eckert, M. R., Vogel, J., and Charpentier, E. (2011). CRISPR RNA maturation by trans-encoded small RNA and host factor RNase III. Nature 471, 602-607.

Deveau, H., Barrangou, R., Garneau, J. E., Labonte, J., Fremaux, C., Boyaval, P., Romero, D. A., Horvath, P., and Moineau, S. (2008). Phage response to CRISPR-encoded resistance in *Streptococcus thermophilus*. J. Bacteriol. 190, 1390-1400.

Garneau, J. E., Dupuis, M. E., Villion, M., Romero, D. A., Barrangou, R., Boyaval, P., Fremaux, C., Horvath, P., Magadan, A. H., and Moineau, S. (2010). The CRISPR/Cas bacterial immune system cleaves bacteriophage and plasmid DNA. Nature 468, 67-71.

Gasiunas, G., Barrangou, R., Horvath, P., and Siksnys, V. (2012). Cas9-crRNA ribonucleoprotein complex mediates specific DNA cleavage for adaptive immunity in bacteria. Proc. Natl. Acad. Sci. U.S.A. 109, E2579-2586.

Goldberg, G. W., Jiang, W., Bikard, D., and Marraffini, L. A. (2014). Conditional tolerance of temperate phages via transcription-dependent CRISPR-Cas targeting. Nature 514, 633-637.

Heler, R., Samai, P., Modell, J. W., Weiner, C., Goldberg, G. W., Bikard, D., and Marraffini, L. A. (2015). Cas9 specifies functional viral targets during CRISPR-Cas adaptation. Nature 519, 199-202.

Jiang, F., Taylor, D. W., Chen, J. S., Kornfeld, J. E., Zhou, K., Thompson, A. J., Nogales, E., and Doudna, J. A. (2016). Structures of a CRISPR-Cas9 R-loop complex primed for DNA cleavage. Science 351, 867-871.

Jiang, W., Bikard, D., Cox, D., Zhang, F., and Marraffini, L. A. (2013). RNA-guided editing of bacterial genomes using CRISPR-Cas systems. Nat. Biotechnol. 31, 233-239.

Jinek, M., Chylinski, K., Fonfara, I., Hauer, M., Doudna, J. A., and Charpentier, E. (2012). A programmable dual-RNA-guided DNA endonuclease in adaptive bacterial immunity. Science 337, 816-821.

Jinek, M., Jiang, F., Taylor, D. W., Sternberg, S. H., Kaya, E., Ma, E., Anders, C., Hauer, M., Zhou, K., Lin, S., et al. (2014). Structures of Cas9 endonucleases reveal RNA-mediated conformational activation. Science 343, 1247997.

Jore, M. M., Lundgren, M., van Duijn, E., Bultema, J. B., Westra, E. R., Waghmare, S. P., Wiedenheft, B., Pul, U., Wurm, R., Wagner, R., et al. (2011). Structural basis for CRISPR RNA-guided DNA recognition by Cascade. Nat. Struct. Mol. Biol. 18, 529-536.

Kleinstiver, B. P., Prew, M. S., Tsai, S. Q., Topkar, V. V., Nguyen, N. T., Zheng, Z., Gonzales, A. P., Li, Z., Peterson, R. T., Yeh, J. R., et al. (2015). Engineered CRISPR-Cas9 nucleases with altered PAM specificities. Nature 523, 481-485.

Kreiswirth, B. N., Lofdahl, S., Betley, M. J., O'Reilly, M., Schlievert, P. M., Bergdoll, M. S., and Novick, R. P. (1983). The toxic shock syndrome exotoxin structural gene is not detectably transmitted by a prophage. Nature 305, 709-712.

Levy, A., Goren, M. G., Yosef, I., Auster, O., Manor, M., Amitai, G., Edgar, R., Qimron, U., and Sorek, R. (2015). CRISPR adaptation biases explain preference for acquisition of foreign DNA. Nature 520, 505-510.

Makarova, K. S., Wolf, Y. I., Alkhnbashi, O. S., Costa, F., Shah, S. A., Saunders, S. J., Barrangou, R., Brouns, S. J., Charpentier, E., Haft, D. H., et al. (2015). An updated evolutionary classification of CRISPR-Cas systems. Nat. Rev. Microbiol. 13, 722-736. Marraffini, L. A., and Sontheimer, E. J. (2008). CRISPR interference limits horizontal gene transfer in staphylococci by targeting DNA. Science 322, 1843-1845.

Nunez, J. K., Kranzusch, P. J., Noeske, J., Wright, A. V., Davies, C. W., and Doudna, J. A. (2014). Cas1-Cas2 complex formation mediates spacer acquisition during CRISPR-Cas adaptive immunity. Nat. Struct. Mol. Biol. 21, 528-534.

Nunez, J. K., Lee, A. S., Engelman, A., and Doudna, J. A. (2015). Integrase-mediated spacer acquisition during CRISPR-Cas adaptive immunity. Nature 519, 193-198.

Samai, P., Pyenson, N., Jiang, W., Goldberg, G. W., Hatoum-Aslan, A., and Marraffini, L. A. (2015). Co-transcriptional DNA and RNA Cleavage during Type III CRISPR-Cas Immunity. Cell 161, 1164-1174.

Shipman, S. L., Nivala, J., Macklis, J. D., and Church, G. M. (2016). Molecular recordings by directed CRISPR spacer acquisition. Science.

Shmakov, S., Abudayyeh, O. O., Makarova, K. S., Wolf, Y. I., Gootenberg, J. S., Semenova, E., Minakhin, L., Joung, J., Konermann, S., Severinov, K., et al. (2015). Discovery and Functional Characterization of Diverse Class 2 CRISPR-Cas Systems. Mol. Cell 60, 385-397.

Wei, Y., Terns, R. M., and Terns, M. P. (2015). Cas9 function and host genome sampling in Type II-A CRISPR-Cas adaptation. Genes Dev. 29, 356-361.

Yosef, I., Goren, M. G., and Qimron, U. (2012). Proteins and DNA elements essential for the CRISPR adaptation process in Escherichia coli. Nucleic Acids Res. 40, 5569-5576.

Example 6

This Example Provides a Description of Experimental Procedures Used to Produce that Data Shown in FIGS. 5-8.

Spacer Acquisition Assay During Phage Infection

Spacer acquisition assays of cells harboring the full CRISPR system of Streptococcus pyogenes were performed as described previously, both in liquid and on plate (Heler et al., 2015). For plate acquisition assays, overnight cultures were launched from single colonies and diluted to equal optical densities. CRISPR arrays were amplified by PCR with primer pairs L400-H050 or L400-H052 (Table 3).

Spacer Acquisition Assay in the Absence of Phage Infection

Spacer acquisition assays were conducted by passaging cultures carrying the full S. pyogenes CRISPR system (expressing wtCas9 or hCas9) in the absence of phage for 10 days. Each day, the cultures were diluted 1:100 in fresh media with appropriate antibiotics. The pCRISPR plasmids had barcoded leader sequences. Spacer acquisition was quantified by PCR amplification of the CRISPR array followed by NGS.

Phage Propagation Assay

Overnight cultures were launched from single colonies. Serial dilutions of a stock of phage ϕNM4γ4 (Goldberg et al., 2014) or ϕ85 (Mazmanian et al., 2000) were spotted on fresh soft heart infusion agar (HIA) lawns of targeting cells containing chloramphenicol 10 μg ml$^{-1}$ and 5 mM $CaCl_2$. Plates were incubated at 37° C. overnight and interference efficiency was measured in plaque forming units (pfu).

Bacterial Growth Curves

Overnight cultures were launched from single colonies and diluted 1:100 in BHI. After 1 hour of growth, optical density at 600 nm (OD600) was measured for each culture, and samples were brought to equal cell densities and loaded into 96-well plates along with ϕNM4γ4 at MOI=1. Measurements were taken every 10 minutes for 24 hours.

Cas9 Target Cleavage Assay

Cas9 was expressed and purified as previously described (Jinek et al., 2012). The I473F Cas9 expression vector was cloned by around-the-horn mutagenic PCR (Moore and Prevelige, 2002). crRNA and tracrRNA were transcribed using T7 RNA polymerase from single-stranded DNA templates and hybridized as previously described (Jinek et al., 2012; Sternberg et al., 2014). L2 oligonucleotides (Table 3) were hybridized to generate the two different target DNA duplexes and native PAGE-purified before 5' radiolabeling using [γ-$^{32}$P]-ATP (Perkin-Elmer) and T4 polynucleotide kinase (New England Biosciences).

Cleavage assays were carried out essentially as previously described (Sternberg et al., 2014). In brief, Cas9 and crRNA:tracrRNA were allowed to form an RNP complex before addition of target DNA. Final concentration of RNP was 100 nM and target was 1 nM. Reactions were incubated at room temperature, and aliquots were taken at 0.25, 0.5, 1, 2, 5, 10, 30, and 60 minutes and quenched by addition of an equal volume of 95% formamide and 50 mM EDTA. Samples were run on 10% urea-PAGE, visualized by phosphorimaging, and quantified using ImageQuant (GE Healthcare).

Plasmid Construction

All cloning was performed using chemically competent S. aureus cells, as previously described (Goldberg et al., 2014). The sequences of all the oligonucleotides used in for plasmid construction are in Table 3. BsaI cloning was used to construct pRH065 and pRH079 by inserting TAG (annealed primers H024-H025 containing compatible BsaI overhangs) and NGG-adjacent (H029-H030) spacers targeting ϕNM4γ4 into pDB114 (Bikard et al., 2014). The mutant cas9 library was constructed via 2-piece Gibson assembly (Gibson et al., 2009) by replacing wild-type cas9 on pRH065 with error-prone cas9 amplicons using primer pairs H294-H295 and H293-H296, respectively. The I473F mutation (codon ATT to TTT) was introduced on pRH065, pRH079, pWJ40 (Goldberg et al., 2014) and pDB114 by around-the-horn PCR (Moore and Prevelige, 2002) with primer pair H103-H104 to create plasmids pRH096, pRH176, pRH180 and pRH305. BsaI cloning was used to construct pRH306, pRH307 and pRH308 by inserting AAG (H546-H547), GAG (H548-H549) and CAG (H550-H551)-adjacent spacers targeting ϕNM4γ4 into pRH305. In addition, mutations R425G (AGA to GGA), I473A (ATT to GCT), K500I (AAA to ATA), S701G (AGT to GGT), P756L (CCA to CTA) and A1032G (GCA to GGA) were each introduced on both pRH065 and pWJ40 by around-the-horn PCR with primer pairs H101-H102, H207-H208, H105-H106, H107-H108, H109-H110 and H111-H112 respectively. The randomized pWJ40 and pRH180 leader-barcoded libraries used for MiSeq were each constructed by 2-piece Gibson assembly with primers pairs H378-H294 and H379-H293.

Plasmid Loss Assays

To assess plasmid loss, cultures carrying the full S. pyogenes CRISPR system (expressing wtCas9 or hCas9) were passaged in the absence of phage for 10 days. Each day, the cultures were diluted 1:100 in fresh media with no antibiotics. At the end of the experiment, dilutions of the cells were plated on plates without antibiotic (to count the total number of cells) and with antibiotic (to count the number of cells that still carried the pCRISPR plasmids).

Cas9 Competition Assays

Plasmids pWJ40 and pRH180 carrying the full S. pyogenes CRISPR system (expressing wtCas9 and hCas9, respectively) were transformed into *S. aureus* RN4220 (no antibiotic resistance) and OS2 (erythromycin resistance), respectively. Overnight cultures of RN4220:pWJ40 and OS2:pRH180 launched from single colonies were diluted 1:100 in BHI. After 1 hour of growth, optical density at 600 nm (OD600) was measured for each culture, and samples were brought to equal cell densities. The two cultures were mixed in a 1:1 ratio and passaged for 5 days. Every day, the mixed culture was diluted 1:100 in fresh media and dilutions of the cells were plated on plates with chloramphenicol (to count the total number of cells) and plates with chloramphenicol and erythromycin (to count the number of cells that carried the hCas9 plasmid).

Protein Sequence Alignments

Amino acid sequences of Cas9 were obtained from the NCBI Protein database and aligned with Clustal Omega (www.ebi.ac.uk/Tools/msa/clustalo/). Alignments were visualized with Jalview (Waterhouse et al., 2009).

REFERENCES FOR THIS EXAMPLE

Bikard, D., Euler, C. W., Jiang, W., Nussenzweig, P. M., Goldberg, G. W., Duportet, X., Fischetti, V. A., and Marraffini, L. A. (2014). Exploiting CRISPR-Cas nucleases to produce sequence-specific antimicrobials. Nat Biotechnol 32, 1146-1150.

Gibson, D. G., Young, L., Chuang, R. Y., Venter, J. C., Hutchison, C. A., 3rd, and Smith, H. O. (2009). Enzymatic assembly of DNA molecules up to several hundred kilobases. Nat Methods 6, 343-345.

Goldberg, G. W., Jiang, W., Bikard, D., and Marraffini, L. A. (2014). Conditional tolerance of temperate phages via transcription-dependent CRISPR-Cas targeting. Nature 514, 633-637.

Heler, R., Samai, P., Modell, J. W., Weiner, C., Goldberg, G. W., Bikard, D., and Marraffini, L. A. (2015). Cas9 specifies functional viral targets during CRISPR-Cas adaptation. Nature 519, 199-202.

Jinek, M., Chylinski, K., Fonfara, I., Hauer, M., Doudna, J. A., and Charpentier, E. (2012). A programmable dual-RNA-guided DNA endonuclease in adaptive bacterial immunity. Science 337, 816-821.

Mazmanian, S. K., Liu, G., Jensen, E. R., Lenoy, E., and Schneewind, 0. (2000). *Staphylococcus aureus* sortase mutants defective in the display of surface proteins and in the pathogenesis of animal infections. Proc Natl Acad Sci USA 97, 5510-5515.

Moore, S. D., and Prevelige, P. E., Jr. (2002). A P22 scaffold protein mutation increases the robustness of head assembly in the presence of excess portal protein. J Virol 76, 10245-10255.

Sternberg, S. H., Redding, S., Jinek, M., Greene, E. C., and Doudna, J. A. (2014). DNA interrogation by the CRISPR RNA-guided endonuclease Cas9. Nature 507, 62-67.

Waterhouse, A. M., Procter, J. B., Martin, D. M., Clamp, M., and Barton, G. J. (2009). Jalview Version 2—a multiple sequence alignment editor and analysis workbench. Bioinformatics 25, 1189-1191.

TABLE 1

Related to FIG. 2. Spacer sequences acquired by wtCas9-expressing cells.

| Strain | Sequence | PAM | Location on φNM4y4 | Strand | SEQ ID NO |
|---|---|---|---|---|---|
| RH71 | ataaataaaaaagttactactcacacacta | agg | 258 | − | 2 |
| RH64 | cgaactaggaagaaaaatcgccatcaattca | agg | 453 | − | 3 |
| RH69 | aatagagatactttatctaacatgatacac | ggg | 805 | + | 4 |
| RH51 | tgatacacgggagaacaaaaccatcctacc | cgg | 827 | + | 5 |
| RH99 | tgatacacgggagaacaaaaccatcctacc | cgg | 827 | + | 6 |
| RH47 | gagaacaaaaccatcctacccggtaataaa | tgg | 837 | + | 7 |
| RH107 | tttattttgcgttagaattgacacctcaaga | agg | 873 | + | 8 |
| RH127 | tttattttgcgttagaattgacacctcaaga | agg | 873 | + | 9 |
| RH57-2 | tttattttgcgttagaattgacacctcaaga | agg | 873 | + | 10 |
| RH57-1 | tttagcgatattaattatgctcgtaagaat | cgg | 1241 | + | 11 |
| RH63 | agtattggaatctgatgaatattcatctct | cgg | 1423 | − | 12 |
| RH40 | aaaaatgttttaacacctattaacgtagtat | tgg | 1448 | − | 13 |
| RH85 | aatattcatcagattccaatactacgttaat | agg | 1461 | + | 14 |
| RH36 | ttcttcgcctctatatgtgttttctggtgt | tgg | 2810 | − | 15 |
| RH109 | acaaattttcttcgcctctatatgtgttttc | tgg | 2816 | − | 16 |
| RH10 | ccaatttagaaatattaatcagagtgcctgt | tgg | 2981 | − | 17 |
| RH42 | agaaaatttatacattgattattcaccaac | agg | 2983 | + | 18 |
| RH7 | gctaagactgtgaagcataatactgctact | agg | 3087 | − | 19 |

TABLE 1-continued

Related to FIG. 2. Spacer sequences acquired by wtCas9-expressing cells.

| Strain | Sequence | PAM | Location on φNM4γ4 | Strand | SEQ ID NO |
|---|---|---|---|---|---|
| RH33 | gctaagactgtgaagcataatactgctact | agg | 3087 | − | 20 |
| RH8 | ttttaagctattcattttaaaaggtcatat | ggg | 3400 | + | 21 |
| RH42 | gtgttctcttcaatccattcatctattgct | tgg | 3502 | − | 22 |
| RH85 | atgaatggattgaagagaacacagacgaac | agg | 3540 | + | 23 |
| RH120 | ggagtaactaatatctgaattgttatcagt | tgg | 3650 | − | 24 |
| RH97 | attagttactccacaaatagaaatagagct | agg | 3698 | + | 25 |
| RH86 | ccacaaatagaaatagagctagggagtttaa | cgg | 3709 | + | 26 |
| RH83 | tagttttttgagtatgcttacttttcttg | tgg | 3822 | − | 27 |
| RH32 | acgaaagcgtctttatctcttgtagcaaacg | tgg | 3934 | − | 28 |
| RH30 | aaataagtctaaaaaaccaacgtttaatgat | tgg | 4197 | + | 29 |
| RH52 | aaataagtctaaaaaaccaacgtttaatgat | tgg | 4197 | + | 30 |
| RH55-2 | gaacgaattgtcagtatgtacagattaat | agg | 4241 | + | 31 |
| RH55-1 | aagaagaatacaaattccactttgttattac | agg | 4283 | + | 32 |
| RH11 | gcattacggacgtagtagaagcaattagaaa | tgg | 4577 | + | 33 |
| RH26-1 | aaaaacaattgattgaattagttactcgatt | agg | 4866 | + | 34 |
| RH44 | tagcttagattttgataccaatgatcttat | tgg | 4917 | + | 35 |
| RH77 | tagcttagattttgataccaatgatcttat | tgg | 4917 | + | 36 |
| RH25 | cggattttcatttattaaaccttacaaaa | agg | 5009 | + | 37 |
| RH115 | tggatatgacgaccaagatttagcgtttta | agg | 5166 | + | 38 |
| RH71 | ataacgacggtacttattccgtcgttgctac | tgg | 5238 | + | 39 |
| RH36 | taatacaggttttacaaaagctttaccat | agg | 5991 | + | 40 |
| RH16-1 | ctttaaatgttttaaaagaatagcatcatt | tgg | 6436 | + | 41 |

TABLE 2

Related to FIG. 2. Spacer sequences acquired by hCas9-expressing cells.

| Strain | Sequence | PAM | Location on φNM4γ4 | Strand | SEQ ID NO |
|---|---|---|---|---|---|
| RH213 | aatagagatactttatctaacatgatacac | ggg | 805 | + | 42 |
| RH214 | tgatacacgggagaacaaaaccatcctacc | cgg | 827 | + | 43 |
| RH177 | gagaacaaaaccatcctacccggtaataaa | tgg | 837 | + | 44 |
| RH193 | agtattggaatctgatgaatattcatctct | cgg | 1423 | − | 45 |
| RH216 | aaaaatgttttaacacctattaacgtagtat | tgg | 1448 | − | 46 |
| RH206 | aatattcatcagattccaatactacgttaat | agg | 1461 | + | 47 |
| RH166 | ttcttcgcctctatatgtgttttctggtgt | tgg | 2810 | − | 48 |
| RH199 | aaataagtctaaaaaaccaacgtttaatgat | tgg | 4197 | + | 49 |

TABLE 2-continued

Related to FIG. 2. Spacer sequences acquired by hCas9-expressing cells.

| Strain | Sequence | PAM | Location on φNM4γ4 | Strand | SEQ ID NO |
|---|---|---|---|---|---|
| RH174 | aataagatcattggtatcaaaatctaagct | agg | 4889 | − | 50 |
| RH195 | cggattttctcatttattaaaccttacaaaa | agg | 5009 | + | 51 |
| RH210 | cggattttctcatttattaaaccttacaaaa | agg | 5009 | + | 52 |
| RH187 | cgacataacgctaatacatgtttgtcatag | tgg | 5695 | − | 53 |
| RH205 | taatacaggttttttacaaaagctttaccat | agg | 5991 | + | 54 |
| RH211 | tttttatttaagtattcgataatttctttata | ggg | 7355 | − | 55 |
| RH202 | tgtatgtcgctttgatacgatccatcaacat | tgg | 8123 | − | 56 |
| RH175 | attagacttttactttccattacttaaatca | tgg | 9043 | + | 57 |
| RH215 | attagacttttactttccattacttaaatca | tgg | 9043 | + | 58 |
| RH164 | ctaatactgttttaattaagttatcgatatc | cgg | 9097 | − | 59 |
| RH185 | atttatatccgatcttatacgaagtaaaga | agg | 13617 | + | 60 |
| RH208 | gcaaagttgagcgatcagtctgatttgatg | agg | 13783 | + | 61 |
| RH200 | ggaatatgatagcaattcaattgcacagta | tgg | 13911 | + | 62 |
| RH203 | aaaatgcaagaattaaactacccaccatat | agg | 14402 | − | 63 |
| RH169 | gataaaatcaaacaacttcacgacgcaataa | cgg | 15028 | + | 64 |
| RH198 | gataaaatcaaacaacttcacgacgcaataa | cgg | 15028 | + | 65 |
| RH197 | cgagtccaacacgtcatcaaattcttttat | agg | 16180 | − | 66 |
| RH168 | atatacacacatactaaacctgaacgatta | agg | 16252 | + | 67 |
| RH209 | tatgtgactctattagagcctcaatatgctt | agg | 16314 | − | 68 |
| RH178 | taagaatatagatccctataatgttatttttgt | tgg | 16769 | + | 69 |
| RH189 | gaatatagatccctataatgttatttttgt | tgg | 16769 | + | 70 |
| RH176 | ctcatcaatatcattctgattggttatttt | ggg | 17669 | − | 71 |
| RH179 | attgaaaaagatacgtatgcacattacaca | agg | 18135 | + | 72 |
| RH204 | ctaagatagctaaagcaatacgtgatgatgt | cgg | 18192 | + | 73 |
| RH196 | gaacacgtgatactcatcgtcatttagatg | ggg | 18365 | + | 74 |
| RH180 | ctaatcctttcgaatgataacgatctaattc | agg | 19067 | − | 75 |
| RH173 | tttgatgaaattttagttgttcagatgtagt | agg | 21085 | − | 76 |
| RH192 | taaactactacgacttaagcaggtgccata | tgg | 21278 | + | 77 |
| RH212 | taaactactacgacttaagcaggtgccata | tgg | 21278 | + | 78 |
| RH201 | aaaaataaggcaactgacagctagatattt | agg | 23282 | + | 79 |
| RH165 | tccatttttgctgttgattcttctatgctatc | cgg | 37541 | − | 80 |
| RH170 | cctacgaatatgaacgacacaaatgattta | ggg | 38151 | + | 81 |

TABLE 3

Oligonucleotides used in this study.

| Name | Sequence | SEQ ID NO |
|---|---|---|
| H024 | aaacaaaaacaaaaatgttttaacacctattaacgg | 82 |
| H025 | aaaaccgttaataggtgttaaaacattttttgttttt | 83 |
| H029 | aaacaaaaatgttttaacacctattaacgtagtatg | 84 |
| H030 | aaaacatactacgttaataggtgttaaaacattttt | 85 |
| H050 | aaaacaaaaagcgcaagaagaaatcaaccagcgca | 86 |
| H052 | aaaactttttacaaattgagttatgttcatataa | 87 |
| H101 | gctattttgagaggacaagaagactttttatcc | 88 |
| H102 | ggataaaagtcttcttgtcctctcaaaatagc | 89 |
| H103 | ggaagtctgaagaaacatttaccccatgg | 90 |
| H104 | ccatggggtaaatgtttcttcagacttcc | 91 |
| H105 | gacaaactttgatataaatcttccaaatgaaaaagtactacc | 92 |
| H106 | ggtagtactttttcatttggaagatttatatcaaagtttgtc | 93 |
| H107 | ccatgatgatggtttgacatttaaagaagac | 94 |
| H108 | gtcttctttaaatgtcaaaccatcatcatgg | 95 |
| H109 | gggcggcataagctagaaaatatcg | 96 |
| H110 | cgatattttctagcttatgccgccc | 97 |
| H111 | gcaagaaataggcaaaggaaccgc | 98 |
| H112 | gcggttcctttgcctatttcttgc | 99 |
| H207 | ggaagtctgaagaaacagctaccccatgg | 100 |
| H208 | ccatggggtagctgtttcttcagacttcc | 101 |
| H293 | gcaaaaatggataagaaatactcaataggc | 102 |
| H294 | tattgagtatttcttatccattttttgcctcc | 103 |
| H295 | aacacgcattgatttgagtcagc | 104 |
| H296 | tcctagctgactcaaatcaatgcg | 105 |
| H372 | nnnnnactaggggcttttcaagactg | 106 |
| H373 | nnnnnactgaagaaatcaaccagcgc | 107 |
| H374 | nnnnnctgaggggcttttcaagactg | 108 |
| H375 | nnnnnctggaagaaatcaaccagcgc | 109 |
| H376 | nnnnntgaaggggcttttcaagactg | 110 |
| H377 | nnnnntgagaagaaatcaaccagcgc | 111 |
| H378 | cagggggcttttcaagactgnnnnnnnnnnngagacaaatagtgcg | 112 |
| H379 | cagtcttgaaaagcccctg | 113 |
| H546 | aaactgaatattcatctctcggtatatataatccg | 114 |
| H547 | aaaacgattatatataccgagagatgaatattca | 115 |
| H548 | aaacccagaagttatgatagctaattcgtcatcag | 116 |
| H549 | aaaactgatgacgaattagctatcataacttctgg | 117 |
| H550 | aaacatgctccaatcgataaacaattagataaacg | 118 |

TABLE 3-continued

Oligonucleotides used in this study.

| Name | Sequence | SEQ ID NO |
|---|---|---|
| H551 | aaaacgtttatctaattgtttatcgattggagcat | 119 |
| L400 | cgaaattttttagacaaaaatagtc | 120 |
| L2 Target | gagtggaaggatgccagtgataagtggaatgccatgtgggctgtcaaaattgagc | 121 |
| L2 RC | gctcaattttgacagcccacatggcattccacttatcactggcatccttccactc | 122 |
| L2 AG PAM | gagtggaaggatgccagtgataagtggaatgccatgtaggctgtcaaaattgagc | 123 |
| L2 AG RC | gctcaattttgacagcctacatggcattccacttatcactggcatccttccactc | 124 |
| L2 crRNA | gugauaaguggaaugccauggguuuuagagcuaugcuguuuug | 125 |
| tracrRNA | ggacagcauagcaaguuaaaauaaggcuaguccguuaucaacuugaaaaaguggcaccgagucggugcuuuuu | 126 |
| L1 sgRNA | gacgcauaaagaugagacgcguuuuagagcuaugcuguuuuggaaacaaaacagcauagcaaguuaaaauaaggcuaguccguuaucaacuugaaaaaguggcaccgagucgugcuuuuuuggauc | 127 |

While the invention has been described through specific embodiments, routine modifications will be apparent to those skilled in the art and such modifications are intended to be within the scope of the present invention.

What is claimed is:

1. An expression vector encoding a Cas9 enzyme comprising a substitution, wherein the substitution is of at least one of the following amino acids: I473 and K500 in SEQ ID NO:1, and wherein relative to a control the Cas9 enzyme exhibits at least one of: i) increased rate of spacer acquisition, or ii) increased cleavage efficiency of targets with NAG protospacer adjacent motifs (PAMs), wherein the control comprises a rate of spacer acquisition, or increased cleavage efficiency of targets with NAG PAMs, produced by a Cas9 enzyme comprising the sequence of SEQ ID NO:1.

2. The expression vector of claim 1, wherein the Cas9 enzyme is a *Streptococcus pyogenes* Cas9 enzyme.

3. The expression vector of claim 1, wherein the substitution comprises I473F.

4. The expression vector of claim 1, wherein the substitution comprises I473F and K500I.

5. Bacteria comprising an expression vector of claim 1.

6. A method of making modified bacteria comprising introducing into the bacteria an expression vector of claim 4.

7. A method comprising contacting bacteria of claim 5 with one or more bacteriophage such that at least one spacer sequence in the genome of the bacteriophage is acquired by the bacteria.

8. The method of claim 7, wherein the bacteria are contacted with a plurality of distinct bacteriophage, and wherein the bacteria acquire a plurality of distinct spacer sequences from the plurality of the bacteriophage, and wherein the number of distinct spacers in the plurality is greater that a control value, and/or the distinct spacers in the plurality are acquired more quickly than for a control value, and wherein the control value comprises a number of distinct spacers, or a rate at which spacers are acquired, obtained by contacting bacteria that express a Cas9 enzyme comprising the sequence of SEQ ID NO:1 with a plurality of distinct bacteriophage.

9. The method of claim 7, wherein the bacteriophage are obtained from a bacterial culture used to produce a food product or a beverage.

10. The method of claim 9, wherein the food product comprises a dairy product.

11. A food product comprising bacteria of claim 5.

12. The food product of claim 11, wherein the food product comprises a dairy product.

13. A method for labeling bacteria with one or more spacer sequences, the method comprising introducing into the bacteria an expression vector of claim 1, and introducing into the bacteria a polynucleotide comprising at least one spacer sequence.

14. The method of claim 13, further comprising determining the sequence of at least one spacer sequence from bacteria that acquired the spacer sequence.

15. A Cas9 enzyme comprising an amino acid substitution, wherein the amino acid substitution is of at least one of the following amino acids: I473 and K500 in SEQ ID NO:1, and wherein relative to a control the Cas9 enzyme exhibits at least one of: i) increased rate of spacer acquisition, or ii) increased cleavage efficiency of targets with NAG protospacer adjacent motifs (PAMs), wherein the control comprises a rate of spacer acquisition, or increased cleavage efficiency of targets with NAG PAMs, produced by a Cas9 enzyme comprising the sequence of SEQ ID NO:1.

16. The Cas9 enzyme of claim 15, wherein the Cas9 enzyme is a *Streptococcus pyogenes* Cas9 enzyme.

* * * * *